United States Patent
Kizuka et al.

(10) Patent No.: US 12,090,053 B2
(45) Date of Patent: Sep. 17, 2024

(54) MEDICAL DEVICE DELIVERY SYSTEM WITH LOCKING SYSTEM

(71) Applicant: EVALVE, INC., Santa Clara, CA (US)

(72) Inventors: Koji Kizuka, Redwood City, CA (US); Gabriel Gonzales, Milpitas, CA (US); Dylan Van Hoven, San Carlos, CA (US); Alexander Chu, Diamond Bar, CA (US); Erik Jagger, Redwood City, CA (US); Scott Mosher, San Francisco, CA (US)

(73) Assignee: EVALVE, INC., Santa Clara, CA (US)

( * ) Notice: Subject to any disclaimer, the term of this patent is extended or adjusted under 35 U.S.C. 154(b) by 0 days.

(21) Appl. No.: 18/130,703

(22) Filed: Apr. 4, 2023

(65) Prior Publication Data

US 2023/0329867 A1    Oct. 19, 2023

Related U.S. Application Data

(63) Continuation of application No. 17/091,881, filed on Nov. 6, 2020, now Pat. No. 11,622,859.

(Continued)

(51) Int. Cl.
*A61F 2/24* (2006.01)
*A61B 17/00* (2006.01)

(52) U.S. Cl.
CPC ...... *A61F 2/2466* (2013.01); *A61B 17/00234* (2013.01); *A61F 2/2427* (2013.01);
(Continued)

(58) Field of Classification Search
CPC .... A61F 2/2466; A61F 2/2427; A61F 2/2439; A61F 2/9517; A61B 17/00234;
(Continued)

(56) References Cited

U.S. PATENT DOCUMENTS

| | | |
|---|---|---|
| 3,378,010 A | 4/1968 | Codling |
| 3,874,388 A | 4/1975 | King |

(Continued)

FOREIGN PATENT DOCUMENTS

| | | |
|---|---|---|
| CA | 2296317 C | 1/2009 |
| EP | 0558031 B1 | 4/1999 |

(Continued)

OTHER PUBLICATIONS

International Search Report dated Feb. 16, 2021 in International Application No. PCT/US2020/059507.
U.S. Appl. No. 16/930,224, filed Jul. 15, 2020, Childs, et al.

*Primary Examiner* — Shaun L David
*Assistant Examiner* — Rachael L Geiger
(74) *Attorney, Agent, or Firm* — SLEMAN & LUND LLP

(57) ABSTRACT

Medical device delivery system including a catheter, handle, lock line handle, and lock line. The catheter includes a proximal end portion and a distal end portion. The handle is coupled to the proximal end portion of the catheter. The lock line handle is releasably coupled to the handle and actuatable between a lock position and an unlock position. The lock line includes a first end portion fixedly coupled to the lock line handle, a second end portion releasably coupled to the lock line handle, and an intermediate portion configured to be releasably coupled to the medical implant disposed proximate the distal end portion of the catheter. Actuating the lock line handle from the lock position toward the unlock position increases tension on the lock line, and actuating the lock line handle from the unlock position toward the lock position decreases tension on the lock line.

20 Claims, 36 Drawing Sheets

Related U.S. Application Data

(60) Provisional application No. 62/932,794, filed on Nov. 8, 2019.

(52) U.S. Cl.
CPC ............. *A61B 2017/00115* (2013.01); *A61B 2017/00243* (2013.01); *A61B 2017/00323* (2013.01); *A61B 2017/00477* (2013.01)

(58) Field of Classification Search
CPC .. A61B 2017/0015; A61B 2017/00243; A61B 2017/00323; A61B 2017/00477
See application file for complete search history.

(56) References Cited

U.S. PATENT DOCUMENTS

| | | |
|---|---|---|
| 4,007,743 A | 2/1977 | Blake |
| 4,055,861 A | 11/1977 | Carpentier |
| 4,327,736 A | 5/1982 | Inoue |
| 4,340,091 A | 7/1982 | Skelton |
| 4,657,024 A | 4/1987 | Coneys |
| 4,693,248 A | 9/1987 | Failla |
| 4,716,886 A | 1/1988 | Schulman |
| 4,795,458 A | 1/1989 | Regan |
| 4,809,695 A | 3/1989 | Gwathmey |
| 4,930,674 A | 6/1990 | Barak |
| 5,002,562 A | 3/1991 | Oberlander |
| 5,069,679 A | 12/1991 | Taheri |
| 5,098,440 A | 3/1992 | Hillstead |
| 5,125,895 A | 6/1992 | Buchbinder |
| 5,147,370 A | 9/1992 | McNamara |
| 5,171,259 A | 12/1992 | Inoue |
| 5,222,963 A | 6/1993 | Brinkerhoff |
| 5,271,544 A | 12/1993 | Fox |
| 5,327,905 A | 7/1994 | Avitall |
| 5,330,501 A | 7/1994 | Tovey |
| 5,334,217 A | 8/1994 | Das |
| 5,363,861 A | 11/1994 | Edwards |
| 5,389,077 A | 2/1995 | Melinyshyn |
| 5,403,326 A | 4/1995 | Harrison |
| 5,425,744 A | 6/1995 | Fagan |
| 5,450,860 A | 9/1995 | O'Connor |
| 5,452,837 A | 9/1995 | Williamson, IV |
| 5,456,400 A | 10/1995 | Shichman |
| 5,456,674 A | 10/1995 | Bos |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop |
| 5,601,574 A | 2/1997 | Stefanchik |
| 5,607,462 A | 3/1997 | Imran |
| 5,607,471 A | 3/1997 | Seguin |
| 5,609,598 A | 3/1997 | Laufer |
| 5,611,794 A | 3/1997 | Sauer |
| 5,636,634 A | 6/1997 | Kordis |
| 5,695,504 A | 12/1997 | Gifford, III |
| 5,713,911 A | 2/1998 | Racenet |
| 5,716,417 A | 2/1998 | Girard |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens |
| 5,810,847 A | 9/1998 | Laufer |
| 5,814,097 A | 9/1998 | Sterman |
| 5,843,178 A | 12/1998 | Vanney |
| 5,849,019 A | 12/1998 | Yoon |
| 5,855,601 A | 1/1999 | Bessler |
| 5,976,159 A | 11/1999 | Bolduc |
| 6,015,417 A | 1/2000 | Reynolds, Jr. |
| 6,048,351 A | 4/2000 | Gordon |
| 6,079,414 A | 6/2000 | Roth |
| 6,117,144 A | 9/2000 | Nobles |
| 6,120,496 A | 9/2000 | Whayne |
| 6,149,658 A | 11/2000 | Gardiner |
| 6,165,183 A | 12/2000 | Kuehn |
| 6,182,664 B1 | 2/2001 | Cosgrove |
| 6,193,734 B1 | 2/2001 | Bolduc |
| 6,200,315 B1 | 3/2001 | Gaiser |
| 6,217,528 B1 | 4/2001 | Koblish |
| 6,269,819 B1 | 8/2001 | Oz |
| 6,290,674 B1 | 9/2001 | Roue |
| 6,312,447 B1 | 11/2001 | Grimes |
| 6,332,880 B1 | 12/2001 | Yang |
| 6,346,074 B1 | 2/2002 | Roth |
| 6,419,696 B1 | 7/2002 | Ortiz |
| 6,461,366 B1 | 10/2002 | Seguin |
| 6,482,224 B1 | 11/2002 | Michler |
| 6,496,420 B2 | 12/2002 | Manning |
| 6,544,215 B1 | 4/2003 | Bencini |
| 6,551,303 B1 | 4/2003 | Van Tassel |
| 6,575,971 B2 | 6/2003 | Hauck |
| 6,599,311 B1 | 7/2003 | Biggs |
| 6,626,930 B1 | 9/2003 | Allen |
| 6,629,534 B1 | 10/2003 | St Goar |
| 6,669,687 B1 | 12/2003 | Saadat |
| 6,695,866 B1 | 2/2004 | Kuehn |
| 6,719,767 B1 | 4/2004 | Kimblad |
| 6,752,813 B2 | 6/2004 | Goldfarb |
| 6,770,083 B2 | 8/2004 | Seguin |
| 6,797,002 B2 | 9/2004 | Spence |
| 6,837,867 B2 | 1/2005 | Kortelling |
| 6,855,137 B2 | 2/2005 | Bon |
| 6,875,224 B2 | 4/2005 | Grimes |
| 6,908,481 B2 | 6/2005 | Cribier |
| 6,926,730 B1 | 8/2005 | Nguyen |
| 7,011,669 B2 | 3/2006 | Kimblad |
| 7,101,395 B2 | 9/2006 | Tremulis |
| 7,112,207 B2 | 9/2006 | Allen |
| 7,125,421 B2 | 10/2006 | Tremulis |
| 7,226,467 B2 | 6/2007 | Lucatero |
| 7,556,632 B2 | 7/2009 | Zadno |
| 7,563,267 B2 | 7/2009 | Goldfarb |
| 7,569,062 B1 | 8/2009 | Kuehn |
| 7,604,646 B2 | 10/2009 | Goldfarb |
| 7,635,329 B2 | 12/2009 | Goldfarb |
| 7,655,015 B2 | 2/2010 | Goldfarb |
| 7,666,204 B2 | 2/2010 | Thornton |
| 7,736,388 B2 | 6/2010 | Goldfarb |
| 7,811,296 B2 | 10/2010 | Goldfarb |
| 7,972,323 B1 | 7/2011 | Bencini |
| 7,981,139 B2 | 7/2011 | Martin |
| 8,057,493 B2 | 11/2011 | Goldfarb |
| 8,062,313 B2 | 11/2011 | Kimblad |
| 8,118,822 B2 | 2/2012 | Schaller |
| 8,216,230 B2 | 7/2012 | Hauck |
| 8,216,256 B2 | 7/2012 | Raschdorf, Jr. |
| 8,303,608 B2 | 11/2012 | Goldfarb |
| 8,343,174 B2 | 1/2013 | Goldfarb |
| 8,500,761 B2 | 8/2013 | Goldfarb |
| 8,734,505 B2 | 5/2014 | Goldfarb |
| 8,740,920 B2 | 6/2014 | Goldfarb |
| 8,945,177 B2 | 2/2015 | Dell |
| 9,011,468 B2 | 4/2015 | Ketai |
| 9,510,829 B2 | 12/2016 | Goldfarb |
| 10,076,415 B1 | 9/2018 | Metchik |
| 10,105,222 B1 | 10/2018 | Metchik |
| 10,123,873 B1 | 11/2018 | Metchik |
| 10,130,475 B1 | 11/2018 | Metchik |
| 10,136,993 B1 | 11/2018 | Metchik |
| 10,159,570 B1 | 12/2018 | Metchik |
| 10,231,837 B1 | 3/2019 | Metchik |
| 10,238,493 B1 | 3/2019 | Metchik |
| 10,245,144 B1 | 4/2019 | Metchik |
| D847,983 S | 5/2019 | Ho |
| 10,314,586 B2 | 6/2019 | Greenberg |
| 10,413,408 B2 | 9/2019 | Krone |
| 10,507,109 B2 | 12/2019 | Metchik |
| 10,517,726 B2 | 12/2019 | Chau |
| 10,524,792 B2 | 1/2020 | Hernandez |
| 10,595,997 B2 | 3/2020 | Metchik |
| 10,646,342 B1 | 5/2020 | Marr |
| 10,779,837 B2 | 9/2020 | Lee |
| D902,403 S | 11/2020 | Marsot |

(56) References Cited

U.S. PATENT DOCUMENTS

| | | |
|---|---|---|
| 10,856,988 B2 | 12/2020 | McNiven |
| 2002/0013571 A1 | 1/2002 | Goldfarb |
| 2002/0183787 A1 | 12/2002 | Wahr |
| 2003/0069593 A1 | 4/2003 | Tremulis |
| 2003/0167071 A1 | 9/2003 | Martin |
| 2004/0034365 A1 | 2/2004 | Lentz |
| 2004/0044350 A1 | 3/2004 | Martin |
| 2004/0049207 A1* | 3/2004 | Goldfarb ............... A61B 50/30 606/139 |
| 2004/0092962 A1* | 5/2004 | Thornton ........... A61B 17/1285 606/139 |
| 2005/0267493 A1 | 12/2005 | Schreck |
| 2007/0038293 A1 | 2/2007 | St Goar |
| 2007/0100422 A1* | 5/2007 | Shumer ................... A61F 2/966 623/1.11 |
| 2012/0065464 A1* | 3/2012 | Ellis ....................... A61B 17/10 600/104 |
| 2017/0042546 A1 | 2/2017 | Goldfarb |
| 2017/0049455 A1 | 2/2017 | Seguin |
| 2017/0056169 A1 | 3/2017 | Johnson |
| 2017/0100250 A1* | 4/2017 | Marsot ................ A61F 2/2466 |
| 2017/0239048 A1 | 8/2017 | Goldfarb |
| 2017/0265994 A1 | 9/2017 | Krone |
| 2018/0021133 A1 | 1/2018 | Barbarino |
| 2018/0036119 A1 | 2/2018 | Wei |
| 2018/0071098 A1 | 3/2018 | Alon |
| 2018/0092661 A1 | 4/2018 | Prabhu |
| 2018/0146964 A1 | 5/2018 | Garcia |
| 2018/0235657 A1 | 8/2018 | Abunassar |
| 2018/0242976 A1 | 8/2018 | Kizuka |
| 2018/0243086 A1 | 8/2018 | Barbarino |
| 2018/0325671 A1 | 11/2018 | Abunassar |
| 2018/0344460 A1 | 12/2018 | Wei |
| 2018/0353181 A1 | 12/2018 | Wei |
| 2018/0360457 A1 | 12/2018 | Ellis |
| 2019/0053803 A1 | 2/2019 | Ketai |
| 2019/0125536 A1 | 5/2019 | Prabhu |
| 2019/0151041 A1 | 5/2019 | Ho |
| 2019/0151089 A1 | 5/2019 | Wei |
| 2019/0159899 A1 | 5/2019 | Marsot |
| 2019/0167197 A1 | 6/2019 | Abunassar |
| 2019/0175182 A1 | 6/2019 | Goldfarb |
| 2019/0183571 A1 | 6/2019 | De Marchena |
| 2019/0209293 A1 | 7/2019 | Metchik |
| 2019/0247187 A1 | 8/2019 | Kizuka |
| 2019/0274831 A1 | 9/2019 | Prabhu |
| 2019/0321597 A1 | 10/2019 | Van Hoven |
| 2019/0343630 A1 | 11/2019 | Kizuka |
| 2019/0350702 A1 | 11/2019 | Hernandez |
| 2019/0350710 A1 | 11/2019 | Ketai |
| 2019/0365536 A1 | 12/2019 | Prabhu |
| 2020/0000473 A1 | 1/2020 | Dell |
| 2020/0060687 A1 | 2/2020 | Hernández |
| 2020/0078173 A1 | 3/2020 | McNiven |
| 2020/0113678 A1 | 4/2020 | McCann |
| 2020/0121460 A1 | 4/2020 | Dale |
| 2020/0121894 A1 | 4/2020 | Prabhu |
| 2020/0187942 A1 | 6/2020 | Wei |
| 2020/0205829 A1 | 7/2020 | Wei |
| 2020/0245998 A1 | 8/2020 | Basude |
| 2020/0261107 A1 | 8/2020 | Cohen |
| 2020/0281591 A1 | 9/2020 | Krone |
| 2020/0297489 A1* | 9/2020 | Bishop ............... A61B 17/0487 |
| 2020/0323528 A1 | 10/2020 | Khairkhahan |
| 2020/0323549 A1 | 10/2020 | Goldfarb |
| 2020/0323634 A1 | 10/2020 | Von Oepen |
| 2020/0360018 A1 | 11/2020 | Dell |
| 2020/0367871 A1 | 11/2020 | Van Hoven |
| 2021/0015614 A1* | 1/2021 | Kizuka ................ A61F 2/2418 |
| 2021/0137680 A1* | 5/2021 | Kizuka ............ A61B 17/00234 |

FOREIGN PATENT DOCUMENTS

| | | |
|---|---|---|
| EP | 1383448 A2 | 1/2004 |
| FR | 2768324 A1 | 3/1999 |
| FR | 2768325 B1 | 11/1999 |
| WO | 9101689 A1 | 2/1991 |
| WO | 9212690 A1 | 8/1992 |
| WO | 94018893 A1 | 9/1994 |
| WO | 9632882 A1 | 10/1996 |
| WO | 9727807 A1 | 8/1997 |
| WO | 9807375 A1 | 2/1998 |
| WO | 9907354 A2 | 2/1999 |
| WO | 9913777 A1 | 3/1999 |
| WO | 9915223 A1 | 4/1999 |
| WO | 0003759 A2 | 1/2000 |
| WO | 0060995 A2 | 10/2000 |
| WO | 0128432 A1 | 4/2001 |
| WO | 03020179 A1 | 3/2003 |
| WO | 03049619 A2 | 6/2003 |
| WO | 2015057289 A1 | 4/2015 |
| WO | 2016178722 A1 | 11/2016 |
| WO | 2018093663 A1 | 5/2018 |

\* cited by examiner

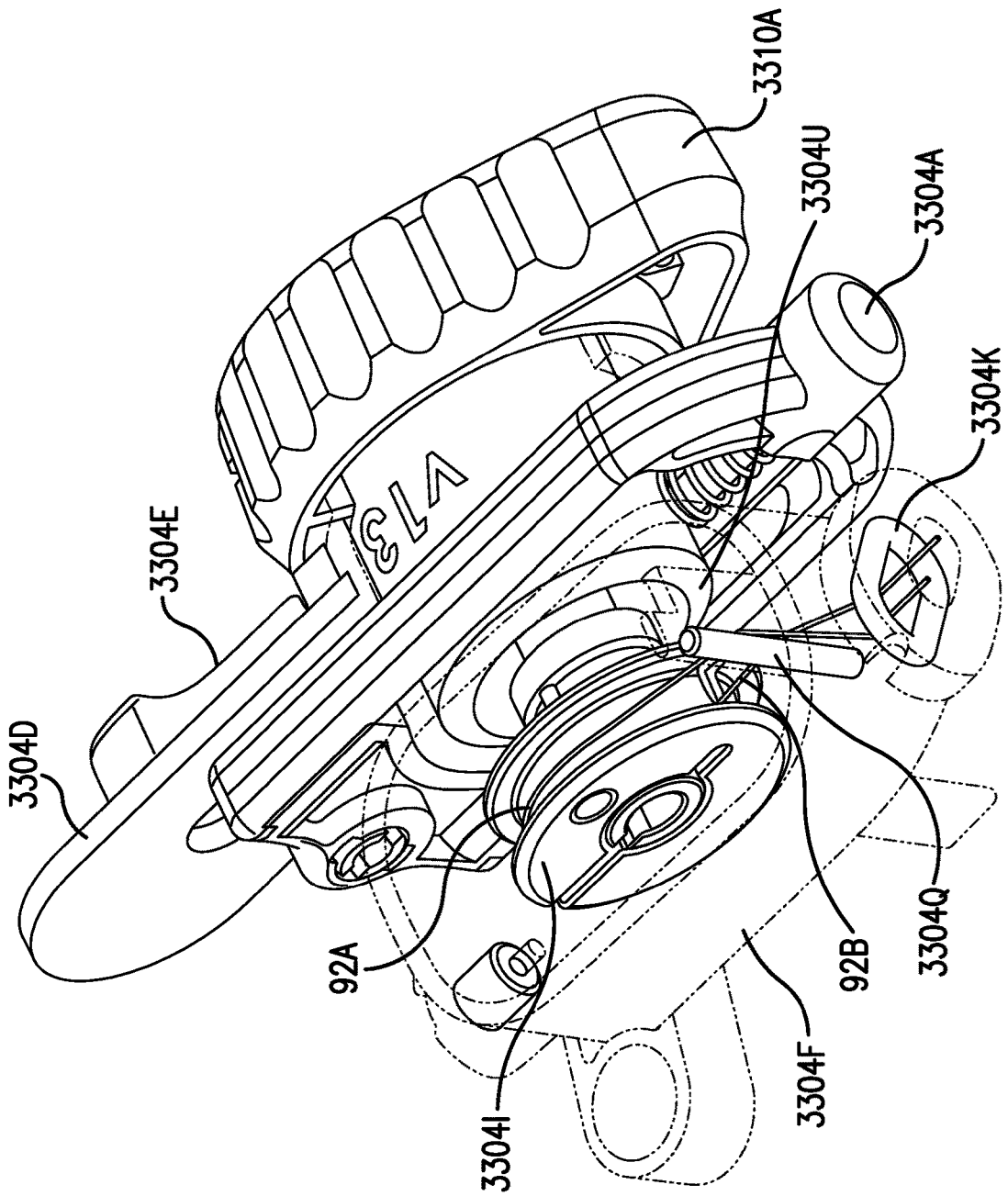

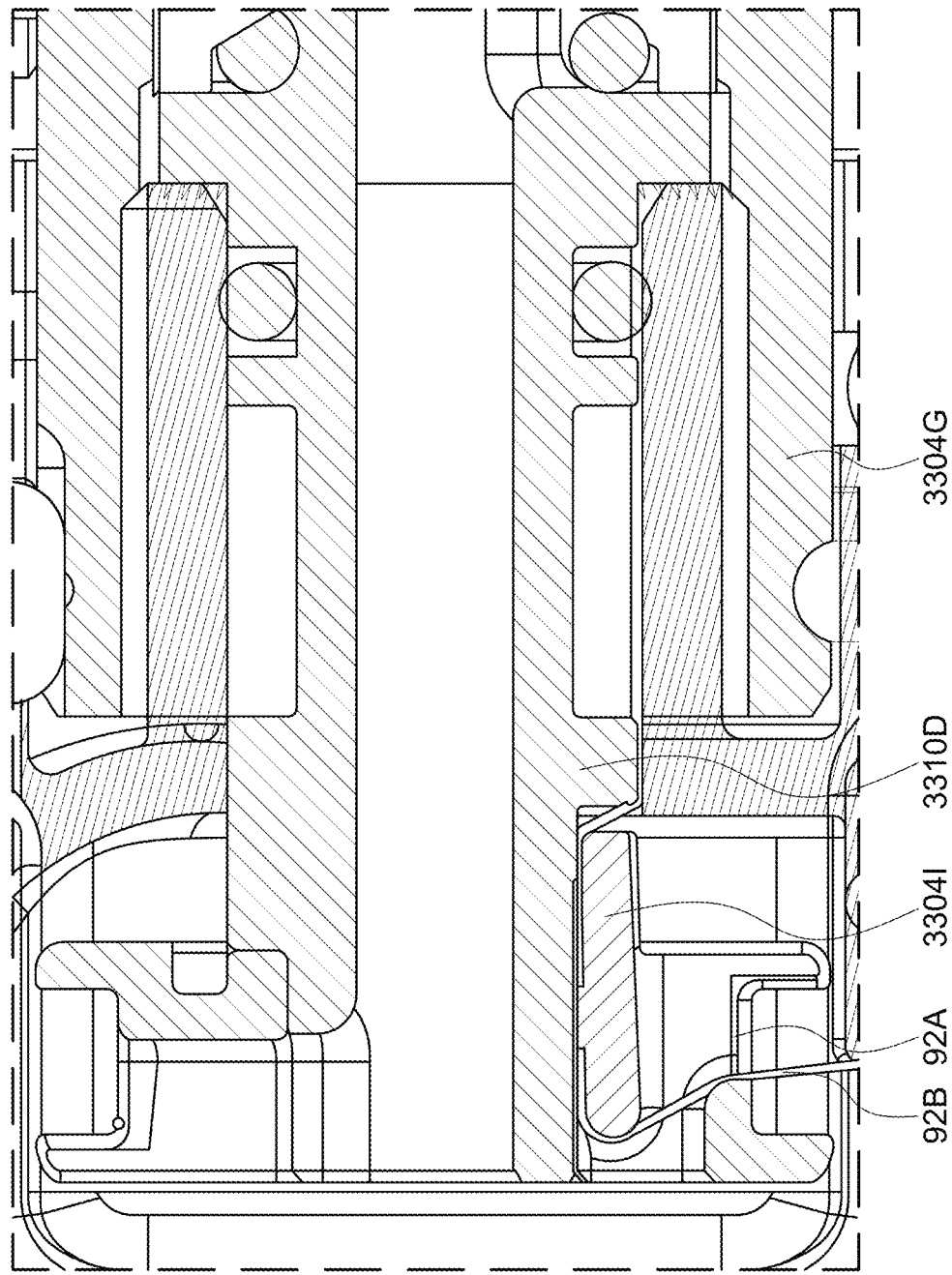

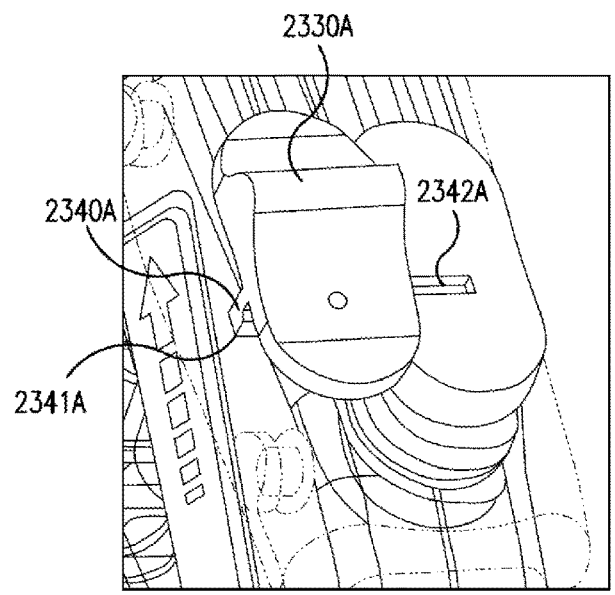
FIG. 22A
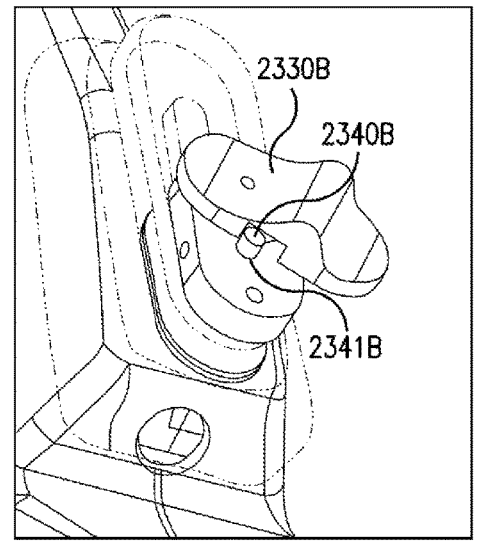
FIG. 22B
FIG. 22C
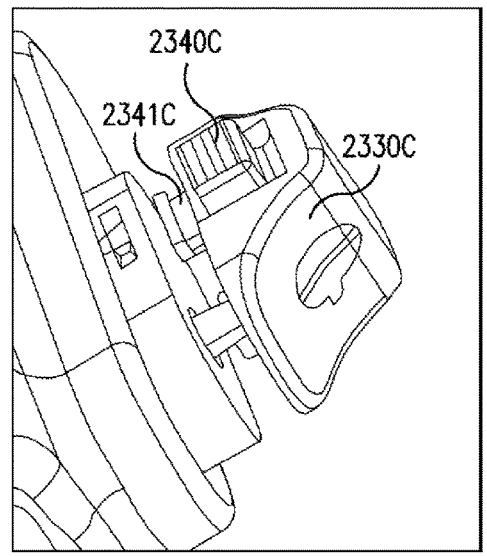

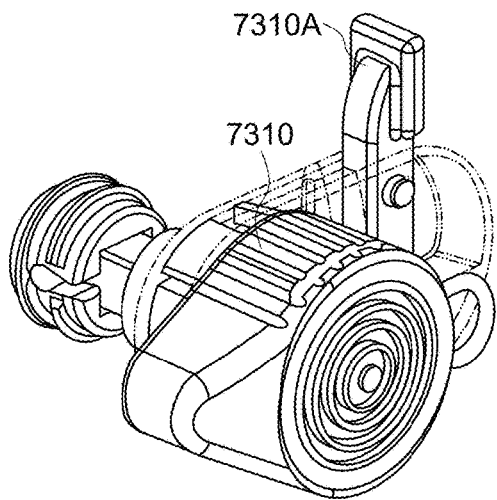 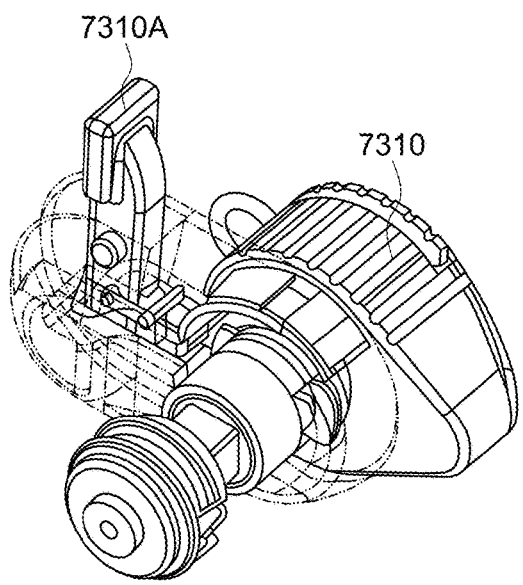
FIG. 31A  FIG. 31B
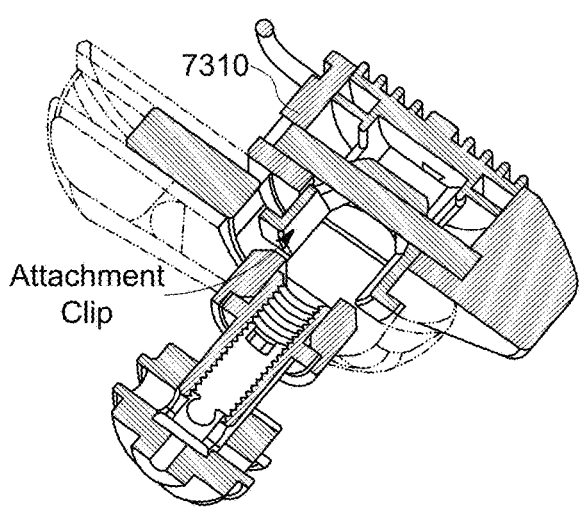 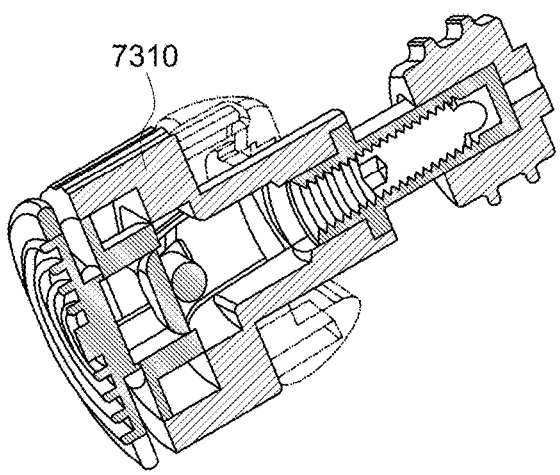
FIG. 31C  FIG. 31D

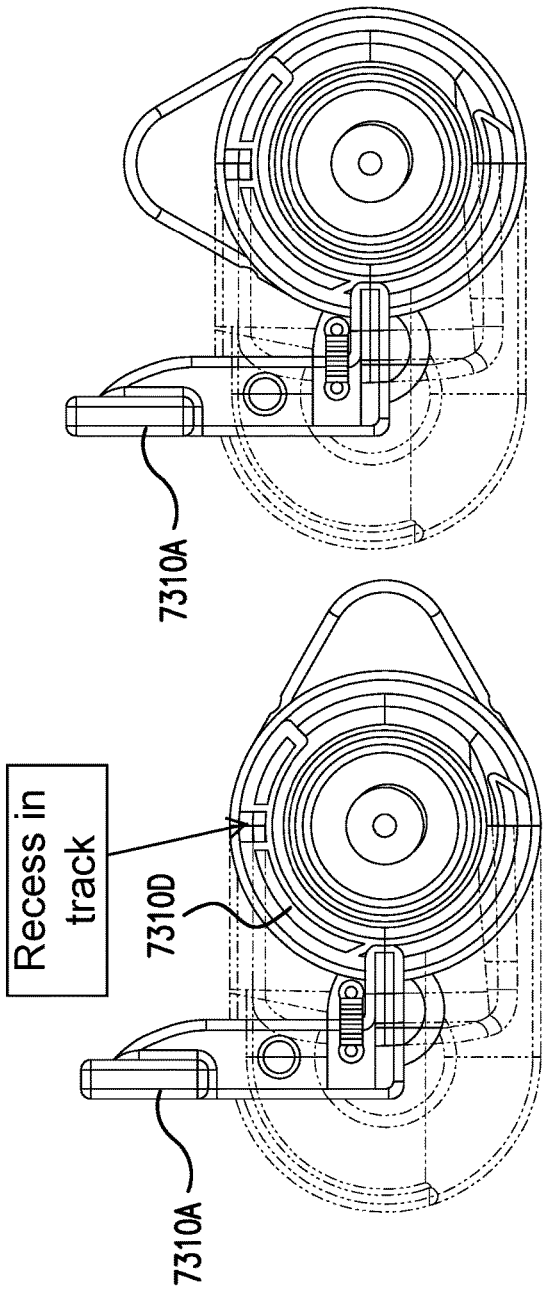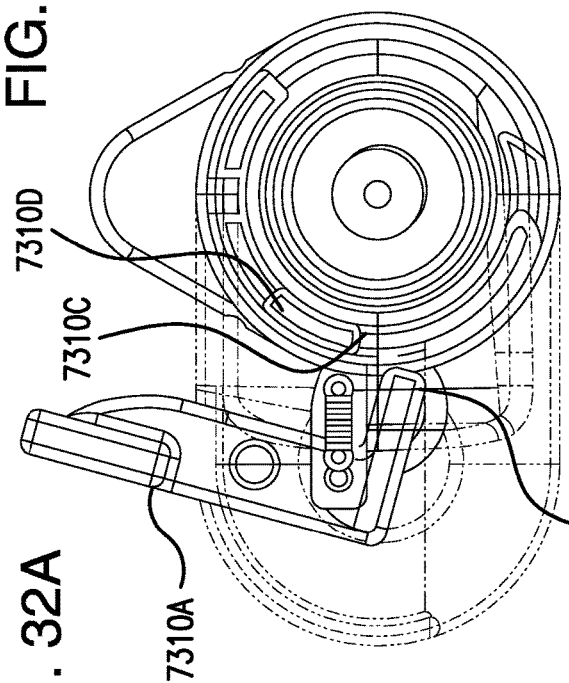

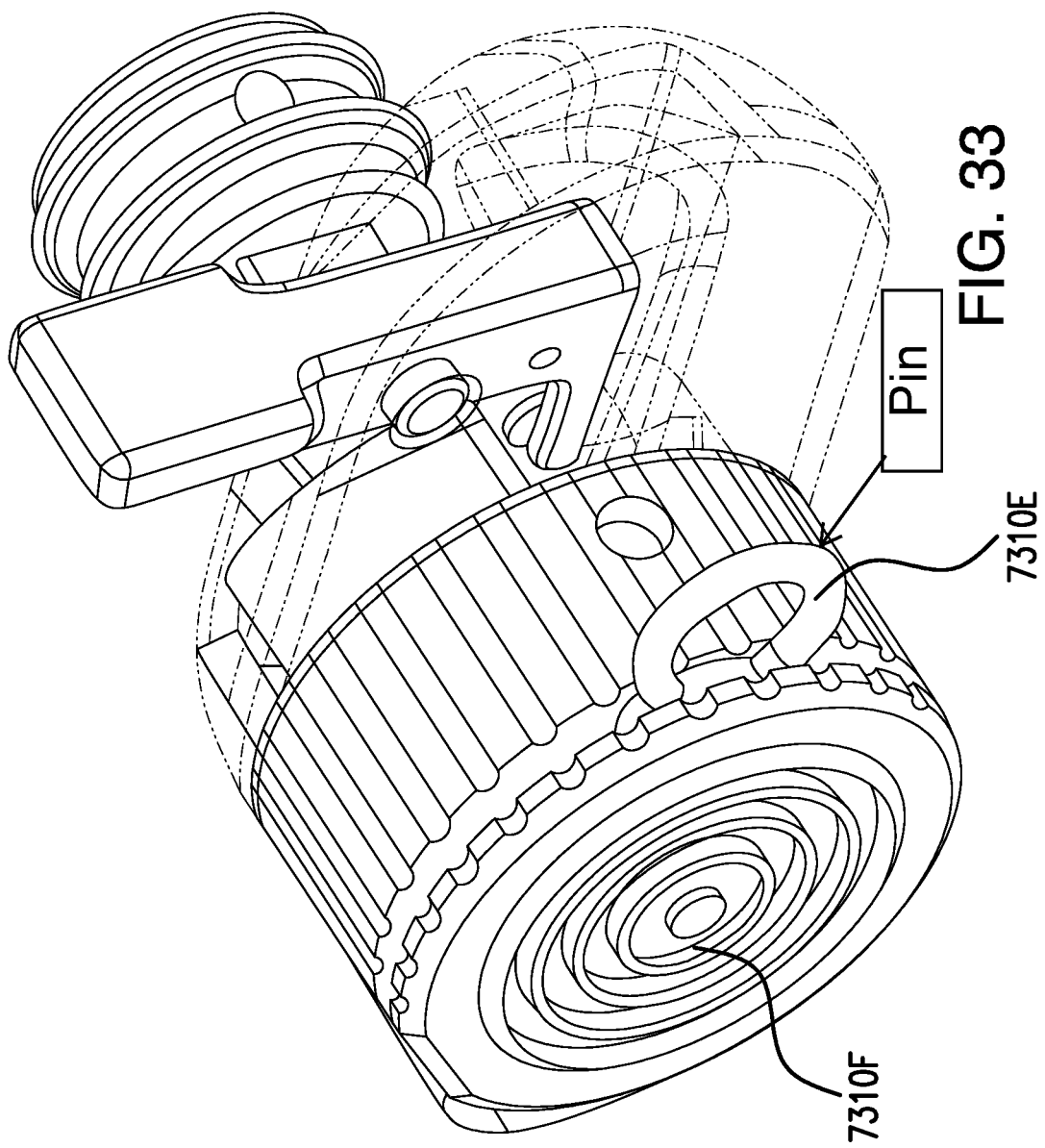

MEDICAL DEVICE DELIVERY SYSTEM WITH LOCKING SYSTEM

CROSS-REFERENCE TO RELATED APPLICATIONS

This application is a continuation of U.S. patent application Ser. No. 17/091,881, filed Nov. 6, 2020, which claims priority to U.S. Provisional Application No. 62/932,794, filed Nov. 8, 2019, the full disclosures of which are incorporated herein by reference in their entireties.

BACKGROUND

Field of Disclosed Subject Matter

The disclosed subject matter is directed to medical devices for endovascular, percutaneous or minimally invasive surgical treatment of bodily tissues, such as tissue approximation or valve repair. More particularly, the present disclosure relates to repair of valves of the heart and venous valves.

Surgical repair of bodily tissues can involve tissue approximation and fastening of such tissues in the approximated arrangement. When repairing valves, tissue approximation includes coapting the leaflets of the valve in a therapeutic arrangement which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of the heart through an incompetent mitral valve into the left atrium. During a normal cycle of heart contraction (systole), the mitral valve acts as a check valve to prevent flow of oxygenated blood from the left ventricle back into the left atrium. As such, as the left ventricle contracts, the oxygenated blood is pumped from the left ventricle into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae connecting the leaflets to the papillary muscles, the papillary muscles, or the left ventricular wall can be damaged or otherwise dysfunctional. Commonly, the valve annulus can be damaged, dilated, or weakened, limiting the ability of the mitral valve to close adequately against the high pressures of the left ventricle.

Description of Related Art

Treatments for mitral valve regurgitation can involve valve replacement or repair including leaflet and annulus remodeling, the latter generally referred to as valve annuloplasty. Another technique for mitral valve repair, which can be referred to as the "bow-tie" or "edge-to-edge" technique, can involve suturing adjacent segments of the opposed valve leaflets together. Preferably, devices and systems for mitral valve repair can be utilized without open chest access, and, rather, can be capable of being performed endovascularly, i.e., delivering fixation devices (e.g., a valve repair clip) using delivery systems advanced to the heart from a point in the patient's vasculature remote from the heart. During endovascular procedures, the fixation devices delivered to the heart can be operated remotely (i.e., from outside the patient's body), for example, the fixation devices can be opened and closed. Additionally, the devices and systems can typically lock the fixation device into a fixed position and unlock the fixation device to allow repositioning (and/or removal if desired), for example, using a lock line extending from the handle (i.e., outside the patient) to the fixation device. Once the tissue has been satisfactorily approximated, the fixation system can be left behind as an implant. As such, there remains a need for ergonomic control of the lock line and release of the lock line to leave the fixation device behind for implantation.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the systems and methods particularly pointed out in the written description and claims hereof, as well as from the appended drawings.

To achieve these and other advantages and in accordance with the purpose of the disclosed subject matter, as embodied and broadly described, the disclosed subject matter is directed to a medical delivery system including a locking system.

In accordance with the disclosed subject matter, a medical delivery device system for delivering a medical implant is provided. The medical device delivery system includes a catheter, handle, lock line handle, and lock line. The catheter includes a proximal end portion and a distal end portion. The handle is coupled to the proximal end portion of the catheter. The lock line handle is releasably coupled to the handle and actuatable between a lock position and an unlock position. The lock line includes a first end portion fixedly coupled to the lock line handle, a second end portion releasably coupled to the lock line handle, and an intermediate portion configured to be releasably coupled to the medical implant disposed proximate the distal end portion of the catheter. Actuating the lock line handle from the lock position toward the unlock position increases tension on the lock line, and actuating the lock line handle from the unlock position toward the lock position decreases tension on the lock line.

In accordance with the disclosed subject matter, the system can include a lock assembly to selectively secure the lock line handle in each of the lock position and unlock position. The lock assembly can include at least one of audible and tactile feedback upon locking. The lock assembly can include a latch-detent lock. The latch of the latch-detent lock can be spring-biased towards a lock position.

In accordance with the disclosed subject matter, the lock line handle can be configured to pivot relative the handle to actuate between the lock position and the unlock position. The lock line handle can include a spool to receive the lock line. The first end portion of the lock line can be coupled to the lock line handle by a swivel-head set screw. The lock line handle can include a pear shape. The lock line handle can be releasably coupled to the handle by one of a snap fit, clip, slide-release, and button-release.

The lock line handle can be configured to translate linearly relative the handle to actuate between the lock position and the unlock position. The lock position can be located distally from the proximal position. The lock line handle can include a T-shape. The lock line handle can include a thumb slide.

The lock line handle can be actuatable from the unlock position toward a third position to further increase tension on the lock line beyond the tension on the lock line in the unlock position. The system can include an override mechanism to selectively prevent activation of the lock line handle from the unlock position to the third position. The second end portion of the lock line is configured to be release when the lock line handle is released from the handle In accordance with the disclosed subject matter, the catheter can define at least one lumen extending between the proximal end portion and the distal end portion. The system can include a shaft having a proximal end portion and a distal end portion, and the shaft can extend through the at least one lumen. The medical implant can be releasably coupled to the distal end portion of the shaft. The system can include an outer catheter having a proximal end portion coupled to the handle and a distal end portion, the outer catheter defining at least one outer-catheter lumen extending between the proximal end portion and the distal end portion; wherein the catheter extends through the outer-catheter lumen.

The medical implant can be an implantable fixation device. The implantable fixation device can include a first arm moveable between a first position and a second position, and a second arm moveable between a first position and a second position. When the lock line handle is in the lock position the first arm and the second arm can be restricted at least from moving from the respective first positions toward the respective second positions. When the lock line handle is in the lock position the first arm and the second arm can move from the respective second positions toward the respective first positions. When the lock line handle is in the unlock position the first arm and the second arm can be moved freely between the respective first positions and second positions. The implantable fixation device can include a first gripping element movable relative to the first arm; and a second gripping element movable relative to the second arm.

BRIEF DESCRIPTION OF THE FIGURES

FIG. 12 is a perspective view of the lock line handle and certain features of the handle of FIG. 6.

FIG. 13A is a cut away view of certain features of the lock line handle and handle of FIG. 6.

FIGS. 22A-C are enlarged detail views of embodiments of slider lock line handles in accordance with the disclosed subject matter.

FIGS. 31A-B are perspective views of a lock line handle in accordance with the disclosed subject matter.

FIGS. 31C-D are cut-away views of the lock line handle of FIG. 31A.

FIGS. 32A-C are cut-away views of the lock line handle of FIG. 31A.

FIG. 33 is a perspective view of the lock line handle of FIG. 31A.

DETAILED DESCRIPTION

Figure 1:
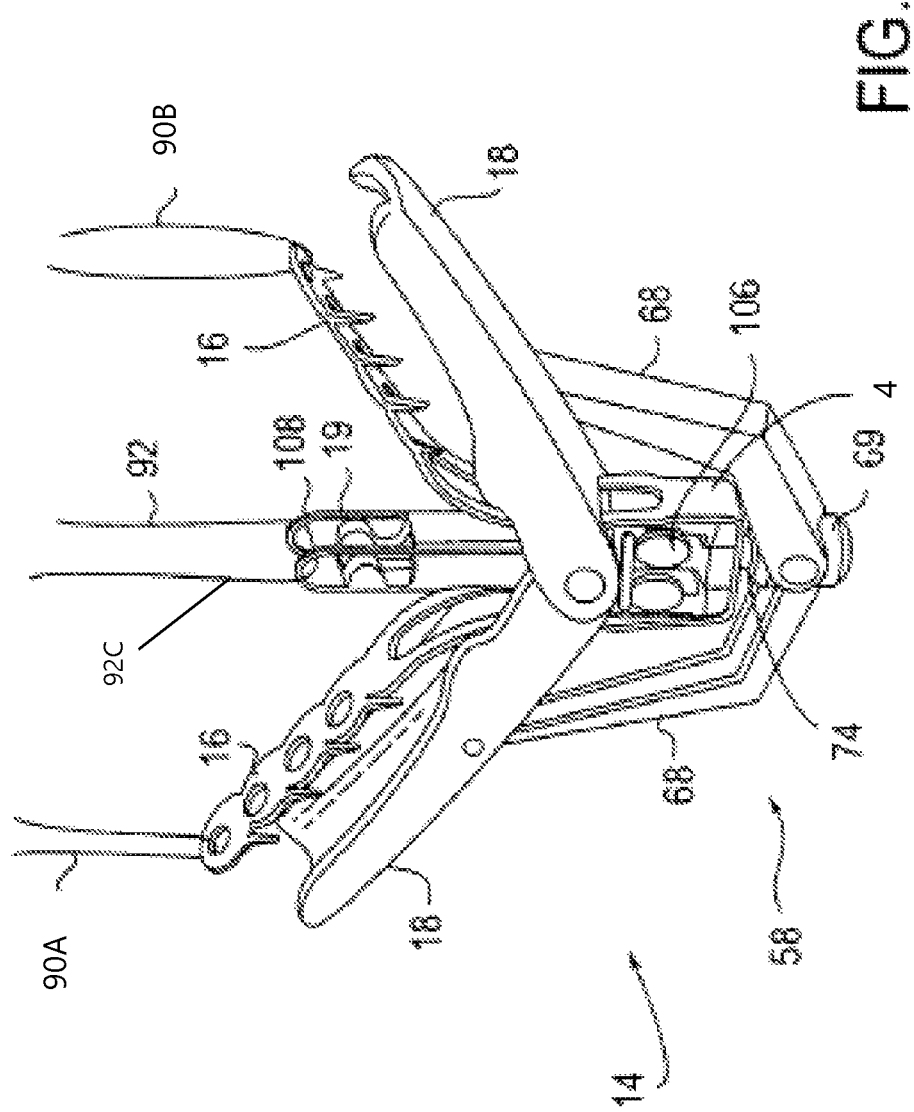
FIG. 1 is perspective view of an exemplary embodiment of a fixation device for use in accordance with the disclosed subject matter.

Reference will now be made in detail to the various exemplary embodiments of the disclosed subject matter, exemplary embodiments of which are illustrated in the accompanying drawings.

Generally, and as set forth in greater detail below, the disclosed subject matter provided herein includes a medical device delivery system for delivering a medical implant, such as a fixation device. The medical device delivery system includes a catheter, handle, lock line handle, and lock line. The catheter includes a proximal end portion and a distal end portion. The handle is coupled to the proximal end portion of the catheter. The lock line handle is releasably coupled to the handle and actuatable between a lock position and an unlock position. The lock line includes a first end portion fixedly coupled to the lock line handle, a second end portion releasably coupled to the lock line handle, and an intermediate portion configured to be releasably coupled to the medical implant disposed proximate the distal end portion of the catheter. Actuating the lock line handle from the lock position toward the unlock position increases tension on the lock line, and actuating the lock line handle from the unlock position toward the lock position decreases tension on the lock line.

The medical device delivery system of the disclosed subject matter can be used for edge-to-edge transcatheter valve repair for patients having various conditions, including regurgitant mitral valves or tricuspid valves. Although described with respect to edge-to-edge repair, the medical device delivery system of the disclosed subject matter can be used with a wide variety of suitable transcatheter delivery systems. Transcatheter (e.g., trans-septal) edge-to-edge valve repair has been established using a fixation device, such as the MitraClip Transcatheter Mitral Valve Repair device. These fixation devices generally are configured to capture and secure opposing native leaflets using two types of leaflet contacting elements. The first element is a subvalvular arm (also known as a distal element or fixation element) to contact the ventricular side of a native leaflet to be grasped. With the arm positioned underneath to stabilize the native leaflet in a beating heart, a second gripping element (also known as a proximal element) can be lowered or moved into contact with the atrial side of the native leaflet to capture the leaflet therebetween. Once each opposing leaflet is captured by a respective arm and gripper element, the fixation device can be closed by moving the arms toward a center of the fixation device such that the leaflets are brought into coaptation, which results in a reduction in valvular regurgitation during ventricular systole. Furthermore, a covering can be provided on the arms and/or gripper elements to facilitate tissue ingrowth with the captured leaflets. Such fixation devices can be delivered to the mitral valve using a delivery system. The delivery system can include control features including, among other things, a locking feature for allowing or inhibiting motion of the distal elements.

Additional details of exemplary fixation devices and delivery systems in accordance with the disclosed subject matter are set forth below. Furthermore, various patents and published applications disclose additional details of such fixation devices and delivery systems and related operations, for example, U.S. Pat. No. 7,226,467 to Lucatero et al., U.S. Pat. No. 7,563,267 to Goldfarb et al., U.S. Pat. No. 7,655,015 to Goldfarb et al., U.S. Pat. No. 7,736,388 to Goldfarb et al., U.S. Pat. No. 7,811,296 to Goldfarb et al., U.S. Pat. No. 8,057,493 to Goldfarb et al., U.S. Pat. No. 8,303,608 to Goldfarb et al., U.S. Pat. No. 8,343,174 to Goldfarb et al., U.S. Pat. No. 8,500,761 to Goldfarb et al., U.S. Pat. No. 8,734,505 to Goldfarb et al., U.S. Pat. No. 8,740,920 to Goldfarb et al., U.S. Pat. No. 9,510,829 to Goldfarb et al., U.S. Pat. No. 7,635,329 to Goldfarb et al., U.S. Pat. No. 8,945,177 to Dell et al., U.S. Pat. No. 9,011,468 to Ketai et al., U.S. Patent Application Publication No. 2017/0042546 to Goldfarb et al., U.S. Patent Application Publication No. 2017/0239048 to Goldfarb et al., U.S. Patent Application Publication No. 2018/0325671 to Abunassar et al., U.S. application Ser. No. 16/930,241 to Kizuka, and U.S. application Ser. No. 16/930,224 to Childs, the entirety of the contents of each of these patents and applications is incorporated herein by reference.

Referring to FIG. 1 for purpose of illustration and not limitation, an exemplary fixation device 14 for fixation of native leaflets of a heart valve is disclosed herein. The fixation device as depicted can include at least gripping elements 16 and arms 18 which can protrude radially outward and can be positionable on opposite sides of tissue, such as leaflets, so as to capture or retain the leaflets therebetween at a single location or along a continuum or range of positions as desired by the user. The gripping elements 16 can be manipulated by gripping element lines 90A, 90B. That is, the gripping elements 16 can be raised and lowered by increasing or decreasing tension on the gripping element lines 90A, 90B. The fixation device 14 is couplable to the shaft of a delivery system (not shown) by a coupling mechanism, a portion of which is shown as coupling member 19. Although a specific arrangement of gripping element lines 90A, 90B, is shown, any suitable arrangement can be used. For example, a single gripping element line manipulate gripping element 16. The coupling mechanism can allow the fixation device 14 to detach and be left behind as an implant to hold the leaflets together in the coapted position. The coupling member 19 can be formed with or connected to housing 4, which can house locking mechanism 106.

The fixation device 14 can include a locking mechanism 106 for locking the device 14 in a particular position, such as an open, closed, or inverted position, or any position therebetween. In accordance with the disclosed subject matter, the locking mechanism 106 can include an unlocking mechanism which can allow the device to be both locked and unlocked. The locking mechanism 106 can be disposed between the coupling member 19 and the base 69 of the actuation mechanism 58. The base 69 can be connected to the legs 68 of the actuation mechanism 58 which can be connected to arms 18. Thus, movement of the legs 68 can move the arms 18 through open, closed and inverted positions. The base 69 can also be fixedly attached to stud 74 which can extend through the locking mechanism 106. The stud 74 can be releasably attached to an actuator rod 64 which passes through coupling member 19 and the shaft of the delivery system. Release of the stud 74 from the actuator rod 64 allows the fixation device 14 to be detached and left behind as an implant.

Lock line 92 is connected with release harness 108 of the locking mechanism 106. The lock line 92 can lock and unlock the locking mechanism 106 as described in greater detail below. The gripping element lines 90A, 90B and lock line 92 can be any suitable material, including wire, nitinol wire, cable, suture or thread. Additionally, gripping element lines 90A, 90B and/or lock line 92 can includes a coating, such as a Parylene®. Parylene® is a vapor deposited pinhole free protective film which is conformal and biocompatible. It is inert and can protect against moisture, chemicals, and electrical charge.

Figure 2:
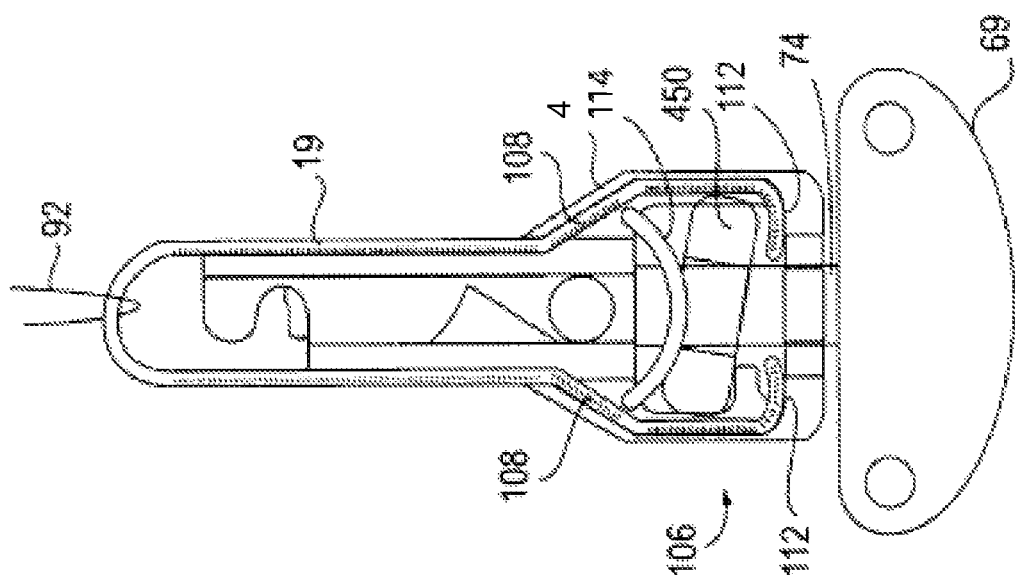
FIG. 2 is side view of a locking system of a fixation device, in accordance with the disclosed subject matter.
Figure 3:
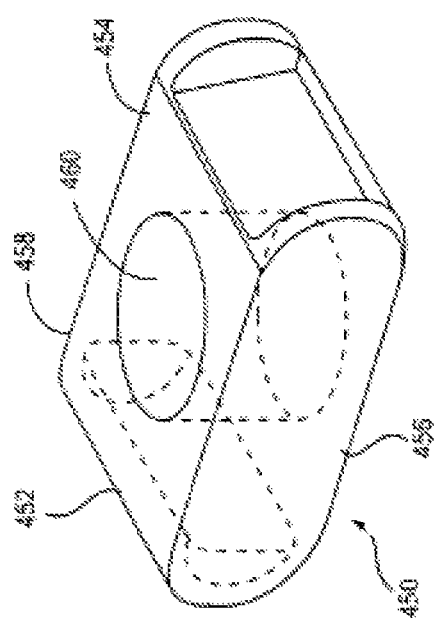
FIG. 3 is a perspective view of the binding plate of the locking system of FIG. 2.
Figure 4:
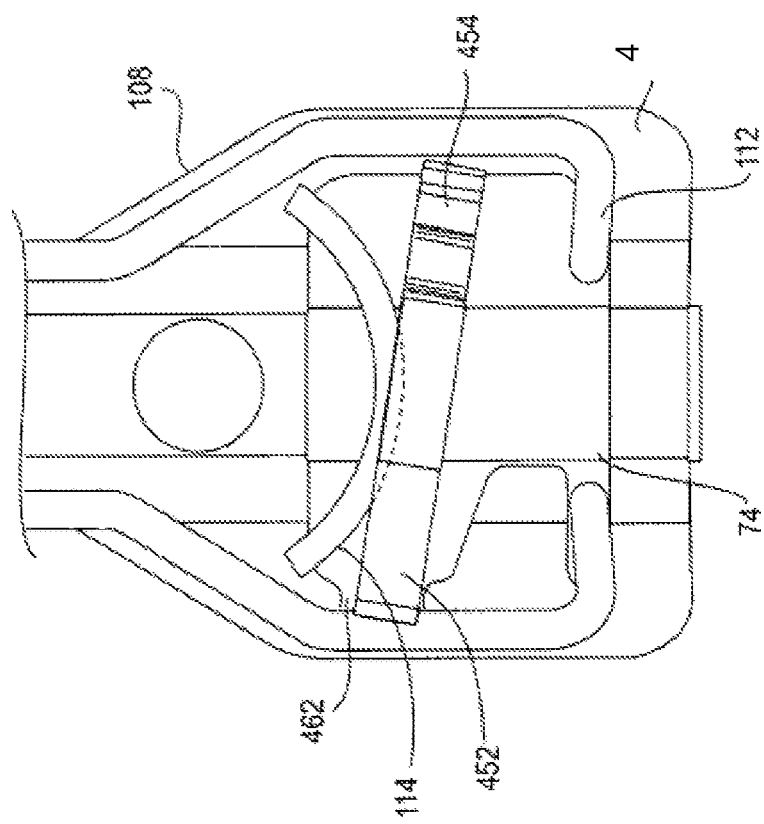
FIG. 4 is an enlarged detail view of a portion of the locking system of FIG. 2.

Referring to FIGS. 2-4 for purpose of illustration and not limitation, an exemplary locking mechanism 106 is provided. The locking mechanism 106 can include a binding lever or binding plate 450. As shown in FIG. 3, for purpose of illustration and not limitation, binding plate 450 can have an oblong shape extending between a first end 452 and a second end 454 with a bottom planar surface 456 and a top planar surface 458. An aperture 460 can be formed between the first end 452 and second end 454 extending from the top planar surface 458 through to the bottom planar surface 456. The binding plate 450 can be positioned within the locking mechanism 106 so that the stud 74 passes through the aperture 460. The first end 452 can be positioned within a notch 462 which can prevent axial movement of the first end 452. However, the second end 454 can be free to move in an axial direction, thereby creating a lever type movement of the binding plate 450. Movement of the second end 454 can be controlled by the associated hooked end 112 of the release harness 108. When an upwards force is applied to the harness 108 by the lock line 92, the hooked end 112 raises the second end 454 of the plate 450 against a spring 114 so that the planar surfaces 456, 458 are substantially perpendicular to the stud 74. This aligns the aperture 460 with the stud 74 allowing free movement of the stud 74. Thus in this state, the locking mechanism 106 is unlocked wherein the stud 74 is free to move the actuation mechanism 58 and therefore the arms 18 to any desired position.

Release of the harness 108 by the lock line 92 can transition the locking mechanism 106 to a lock position. By releasing the upwards force on the second end 452 of the binding plate 450, the spring 114 can force the second end 452 downwards and can wedge the aperture 460 against the stud 74. This can restrict motion of the stud 74, which in turn can lock the actuation mechanism 58 and therefore arms 18 in place. Binding plate 450 can have any suitable form to function as described hereinabove. For example, the plate 450 can include a variety of shapes with or without planar surfaces 456, 458 and/or aperture 460 can be of a variety of shapes and positioned in a variety of locations. Further, any number of binding plates 450 can be present. Each binding plate 450 can provide an additional biding location which can enhance lock performance.

Although this disclosures describes specific designs for the binding plate 450, any suitable binding plate 450 is contemplated. For example, the binding plate 450 can be shaped without an aperture 460. In such embodiments, the binding plate 450 can be shaped to at least partially surround the stud 74, such as having a notch, inlet or hook-shape through which the stud 74 can pass. Thus, the binding plate 450 can function in the same manner as described above wherein the portion at least partially surrounding the stud 74 can engages the stud 74 for locking and disengages the stud 74 for unlocking.

The biding plate 450 and the stud 74 can be any suitable materials. For example, binding plate 450 can have a higher hardness than the stud 74. Alternatively, binding plate 450 can include a flexible or semi-flexible material. Such flexibility can allow a slight movement of the stud 74 in the proximal and distal directions, therefore allowing slight movement of the arms 18 when the locking mechanism is in the lock position. Although this application This can allow the fixation device 14 to adjust in response to dynamic cardiac forces.

Locking mechanism 106 can allow the fixation device 14 to be incrementally moved toward the closed position while locked. Movement toward the closed position is achieved by retracting or pulling the stud 74 in the proximal direction so that the arms 18 approach each other. Retraction of the stud 74 draws the binding plate 450 toward a horizontal position, aligning the aperture with the stud 74 and thus allowing movement. In contrast, extension or pushing of stud 74 in the distal direction can be resisted by further wedging the binding plate 450 against the stud 74. Once the final placement is determined, the lock line 92 and proximal element lines 90A, 90B can be removed and the fixation device can be left behind. Although this disclosure describes specific designs for the lock mechanism, any suitable lock mechanism is contemplated. Additional details and exemplary locking mechanisms are provided in U.S. Pat. No. 8,343,174 to Goldfarb et al., the entirety of the contents of which is incorporated herein by reference.

Figure 5:
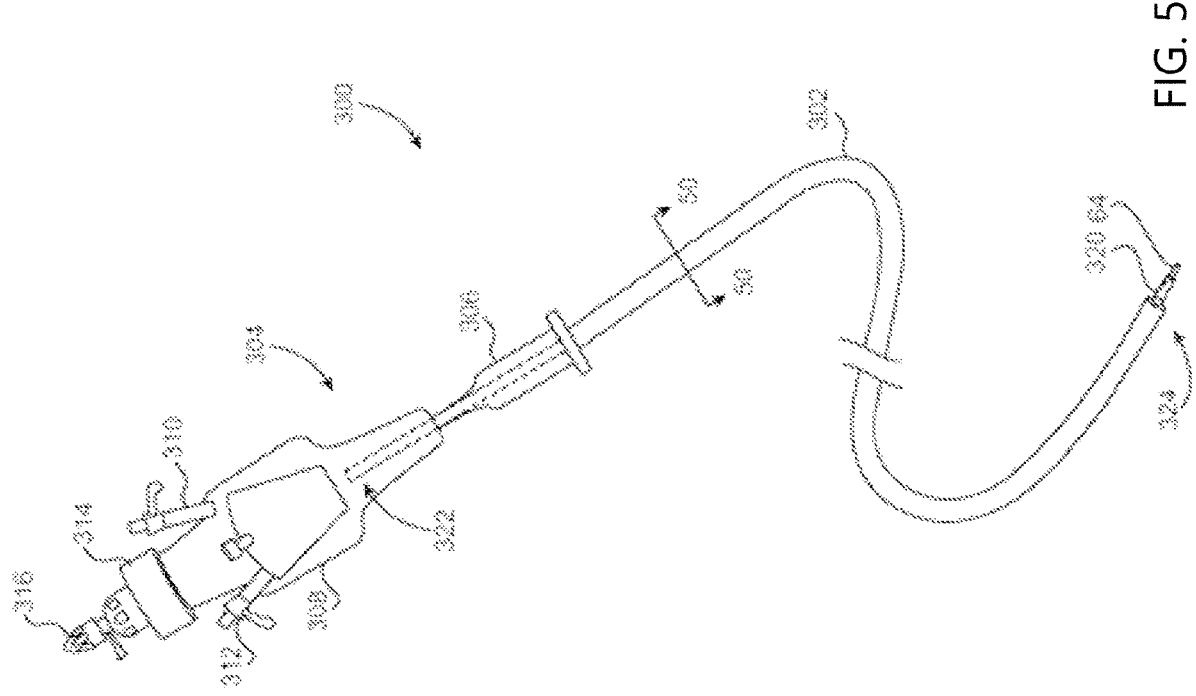
FIG. 5 is a perspective view of an exemplary embodiment of a delivery device for use in accordance with the disclosed subject matter.

Referring to FIG. 5 for purpose of illustration and not limitation, an exemplary delivery device 300 is provided for delivery of a fixation device as disclosed. That is, the delivery device 300 can be used to introduce and position a fixation device as described above. The delivery device 300 can include a shaft 302, having a proximal end 322 and a distal end 324, and a handle 304 attached to the proximal end 322. A fixation device (not shown) can be removably coupleable to the distal end 324 for delivery to a site within the body, for example, the mitral valve. Thus, extending from the distal end 324 is a coupling structure 320 for coupling with a fixation device 104. Also extending from the distal end 324 is an actuator rod 64. The actuator rod 64 is connectable with the fixation device 14, for example to stud 74, and can act to manipulate the fixation device 14, for example, opening and closing the arms 18. Handle 304 of the delivery device 300 is shown, including main body 308, proximal element line handle 312, the lock line handle 310, the actuator rod control 314 and the actuator rod handle 316, among other features. The handle 304 is supported by the support base 306 which is connected to handle 1057 (see FIG. 35).

Lock line (or lines) 92 can pass through at least one lumen of shaft 302 between the lock line handle 310 and the locking mechanism 106. The lock line 92 can engage the release harness 108 of the locking mechanism 106 to lock and unlock the locking mechanism 106 as described above. The lock line 92 can engage the release harness 108 in various arrangements, for example, as shown in FIG. 1. Additional details and exemplary lock line coupling with the fixation device 14 is provided in U.S. Pat. No. 7,563,267 to Goldfarb et al., the entirety of the contents of which is incorporated herein by reference.

Figure 6:
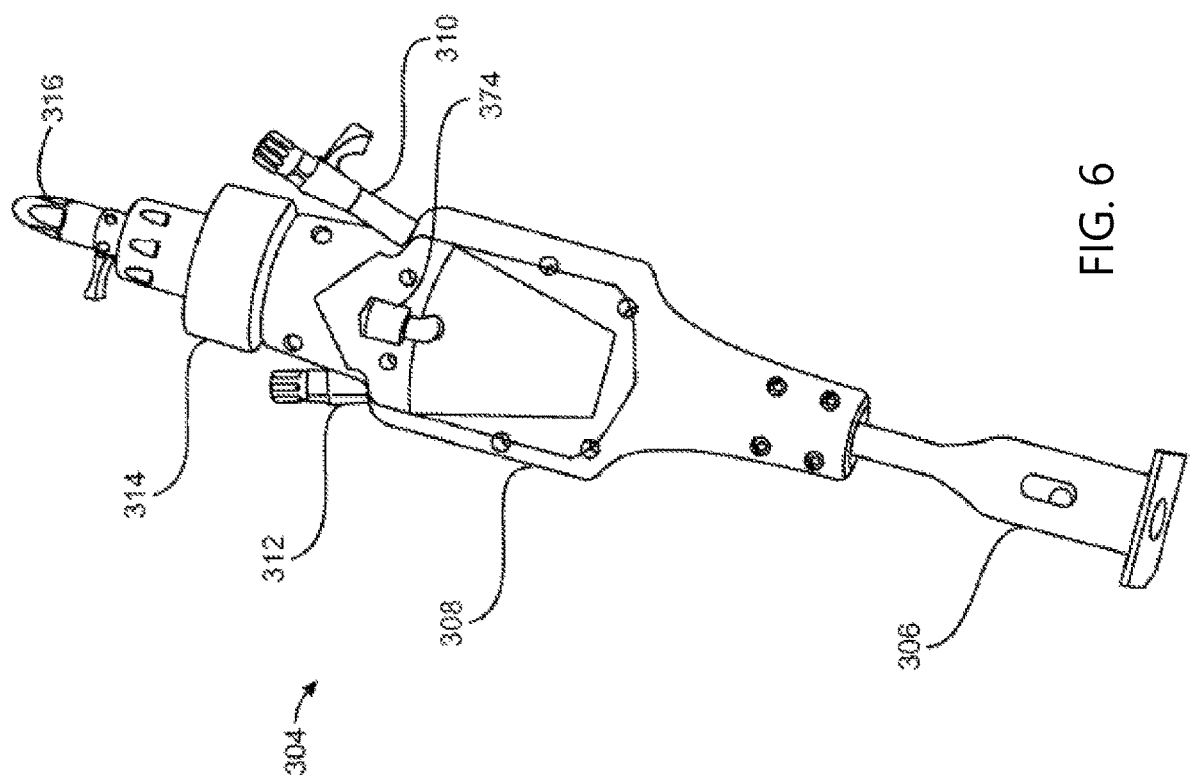
FIG. 6 is an enlarged view of the handle of the delivery device of FIG. 5.
Figure 7:
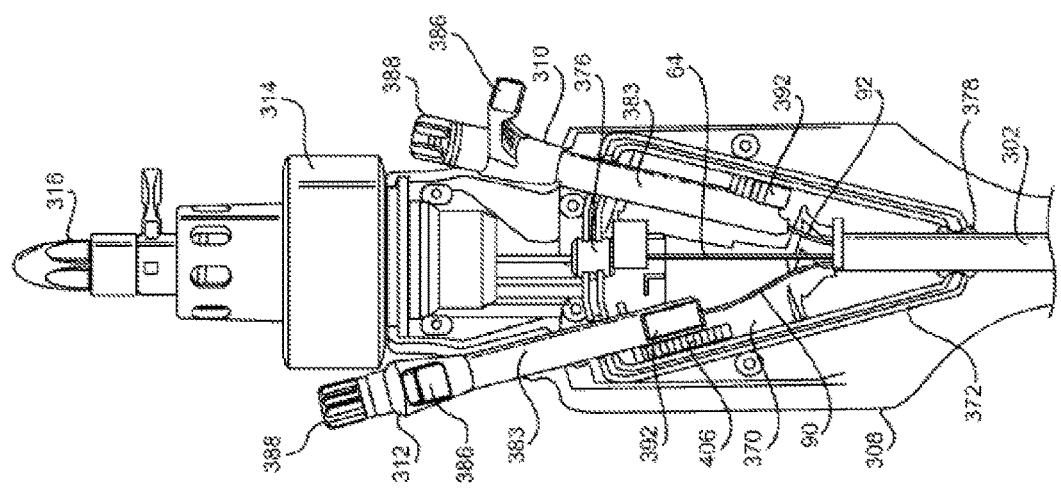
FIG. 7 is a cut-away view of the handle of FIG. 6.
Figure 8:
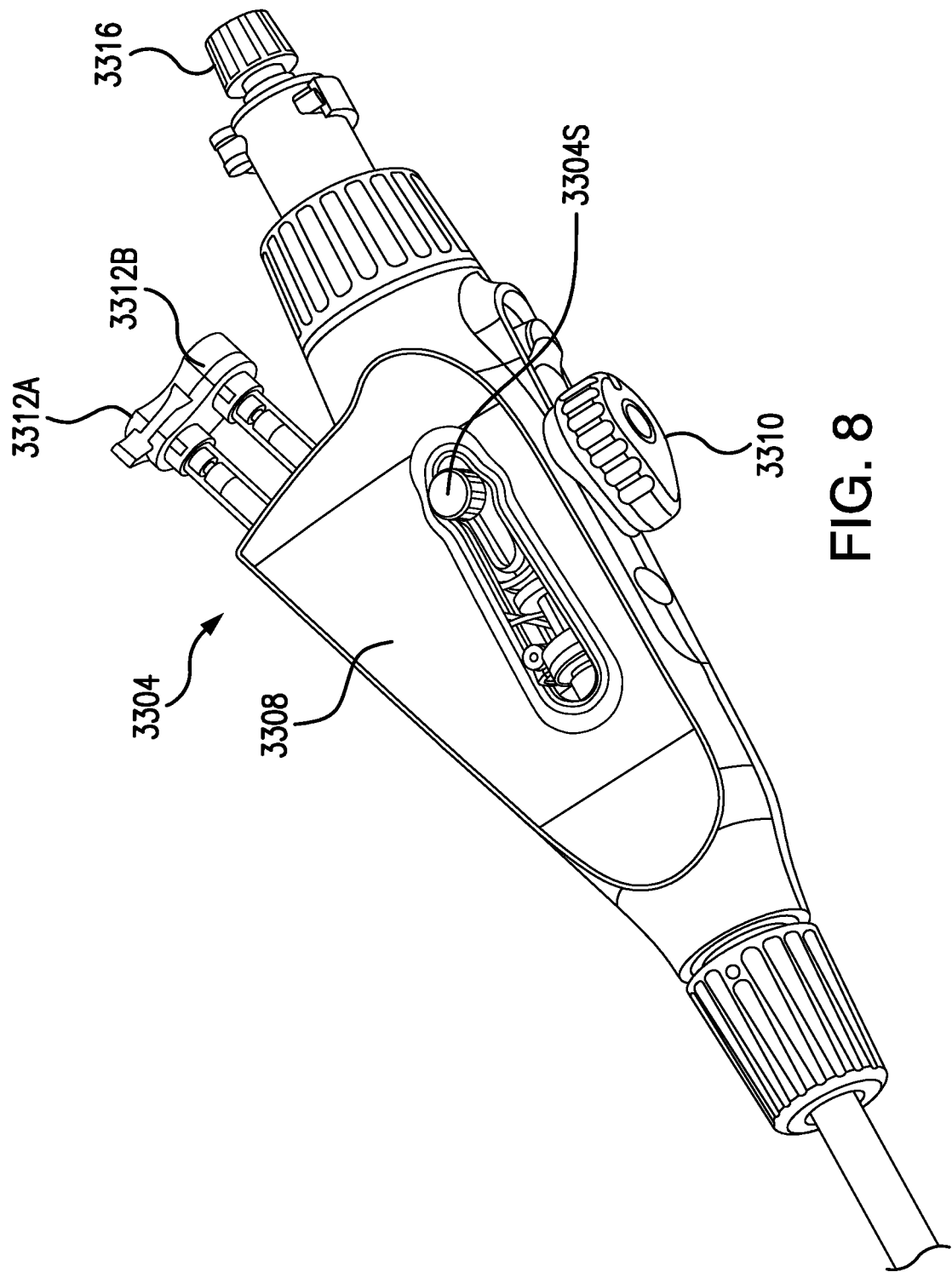
FIG. 8 is an enlarged view of a handle including a lock line handle in accordance with the disclosed subject matter.

Referring to FIGS. 6 and 7 for purpose of illustration and not limitation, actuator rod handle 316, actuator rod control 314, gripping element line handle 312, and lock line handle 310 can all be joined with the main body 318 of handle 304. The handle 304 can include a support base 306 connected with the main body 308. The main body 308 can be slidable along the support base 306 to provide translation of the shaft 302 and the main body 308 is rotateable around the support base 306 to rotate the shaft 302.

FIG. 7 provides a partial cross-sectional view of body 308 of the handle 304 depicted in FIG. 6. As shown in FIG. 7, the main body 308 can include a sealed chamber 370 within which the actuator rod 64, gripping element lines 90A, 90B, and lock line 92 can be guided into the shaft 302. The sealed chamber 370 can be in fluid communication with the inner lumen of the shaft 302 and can be filed with saline and flushed with heparin or heparinized saline. The sealed chamber 370 can have a seal 372 along its perimeter to prevent leakage and the introduction of air to the chamber 370. Air can be bled from the chamber 370 by one or more luers 374 which pass through the main body 308 into the chamber 370 as illustrated in FIG. 6. As shown in FIG. 6, the handle 304 can include two luers 374, one on each side of the main body 308 (the second luer is hidden from view in FIG. 6). The sealed chamber 370 can also have various additional seals, such as an actuator rod seal 376 which can surround the actuator rod 64 where the actuator rod 64 enters the sealed chamber 370, and a shaft seal 378 which can surround the shaft 302 where the shaft 302 enters the sealed chamber 370.

Lock line 92 can be extended, retracted, loaded with various amounts of tension, or removed using the lock line handle 310. Likewise, gripping element lines 90A, 90B can be extended, retracted, loaded with various amounts of tension, or removed using the gripping element line handle 312. Although particular handle 304 including lock line handle 310 and gripping element line handle 312 are shown in FIGS. 5-7, a variety of designs can be implemented to manipulate the appropriate lines.

Referring to FIGS. 8-19, for purpose of illustration and not limitation, handle 3304 can include one or more features described above with regard to handles. For example, handle 3304 can include a main body 3308, a lock line handle 3310, gripping element line handles 3312A, 3312B, and actuator rod handle 3316. The gripping element line handles 3312A, 3312B can be used to independently operate each gripping element line 90A, 90B (FIG. 1), respectively. Additional details and exemplary gripping element line handles are provided in U.S. application Ser. No. 16/930,241 to Kizuka et al., the entirety of the contents of which is incorporated herein by reference. Actuator rod handle 3316 can operate the actuator rod 64. Lock line handle 3310 can operate lock line 92. Lock line handle 3310 can be releasably coupled to the main body 3308. Lock line 92 can have a first end portion 92A (FIG. 13A) fixedly coupled to the lock line handle 3310 and a second end portion 92B (FIG. 13A) releasably coupled to the lock line handle 3310. An intermediate portion 92C (FIG. 1) of the lock line 92 can be configured to engage the release harness 108 in various arrangements, for example, as shown in FIG. 1.

Figure 9:
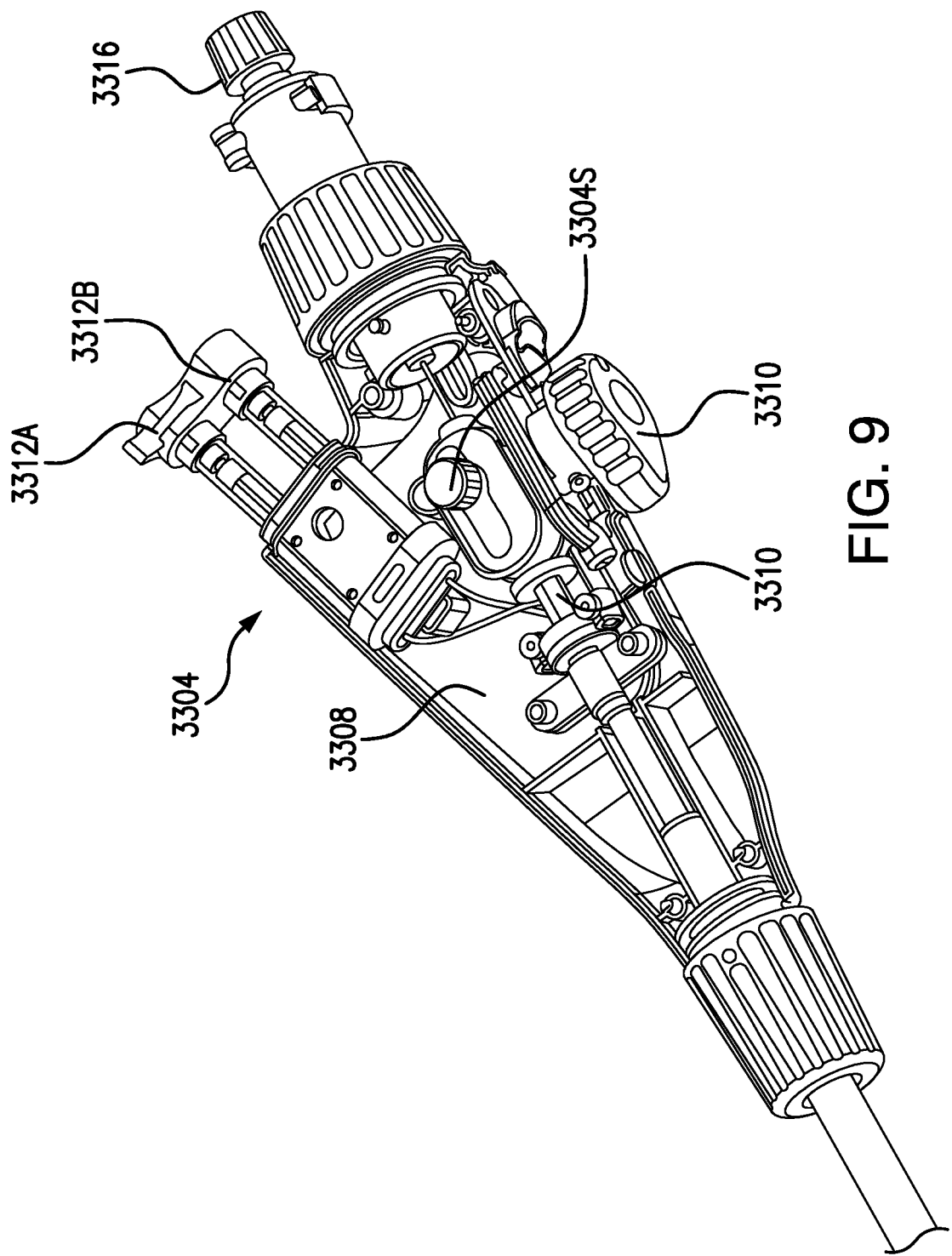
FIG. 9 is a cut-away view of the handle of FIG. 8.
Figure 10:
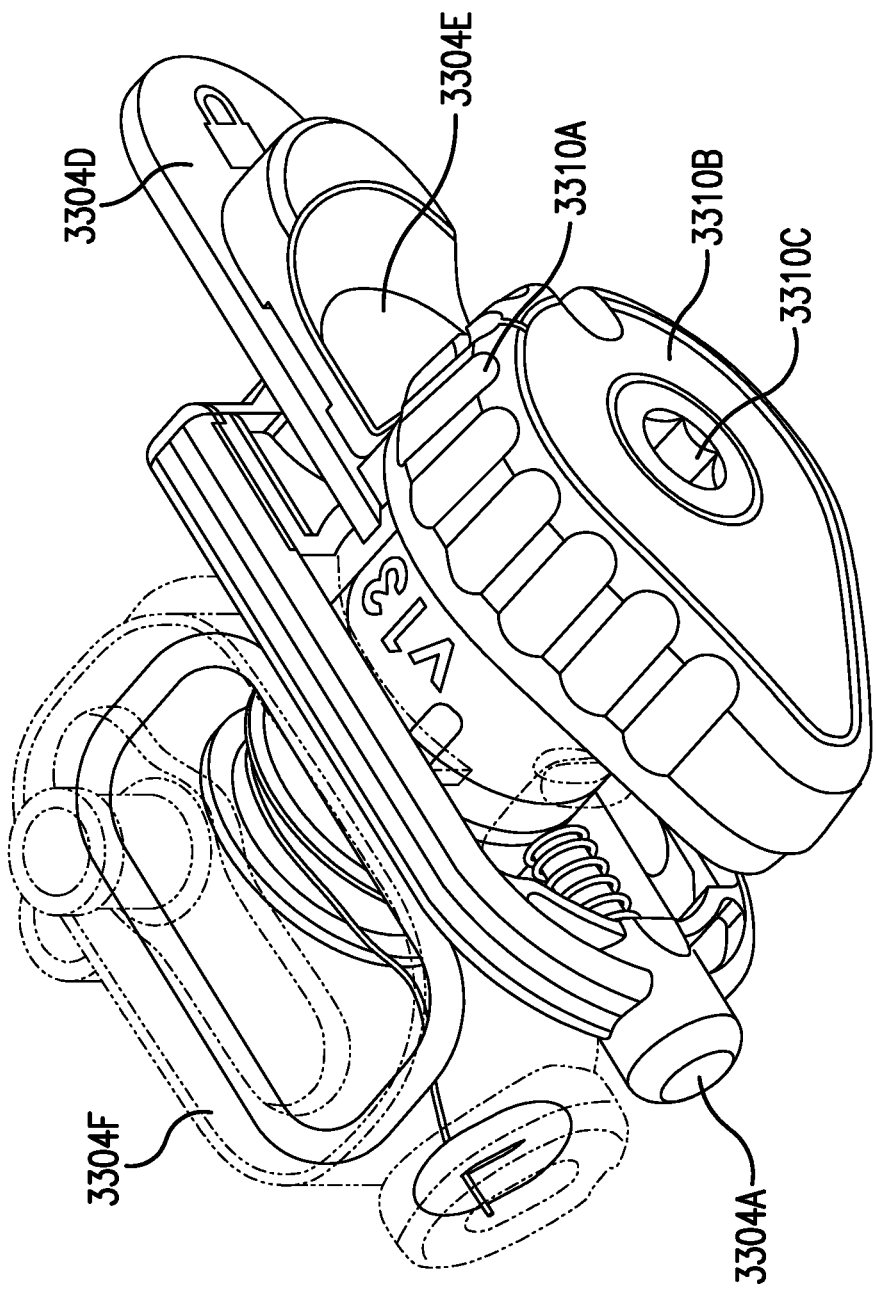
FIG. 10 is a perspective view of the lock line handle and certain features of the handle of FIG. 6.
Figure 11:
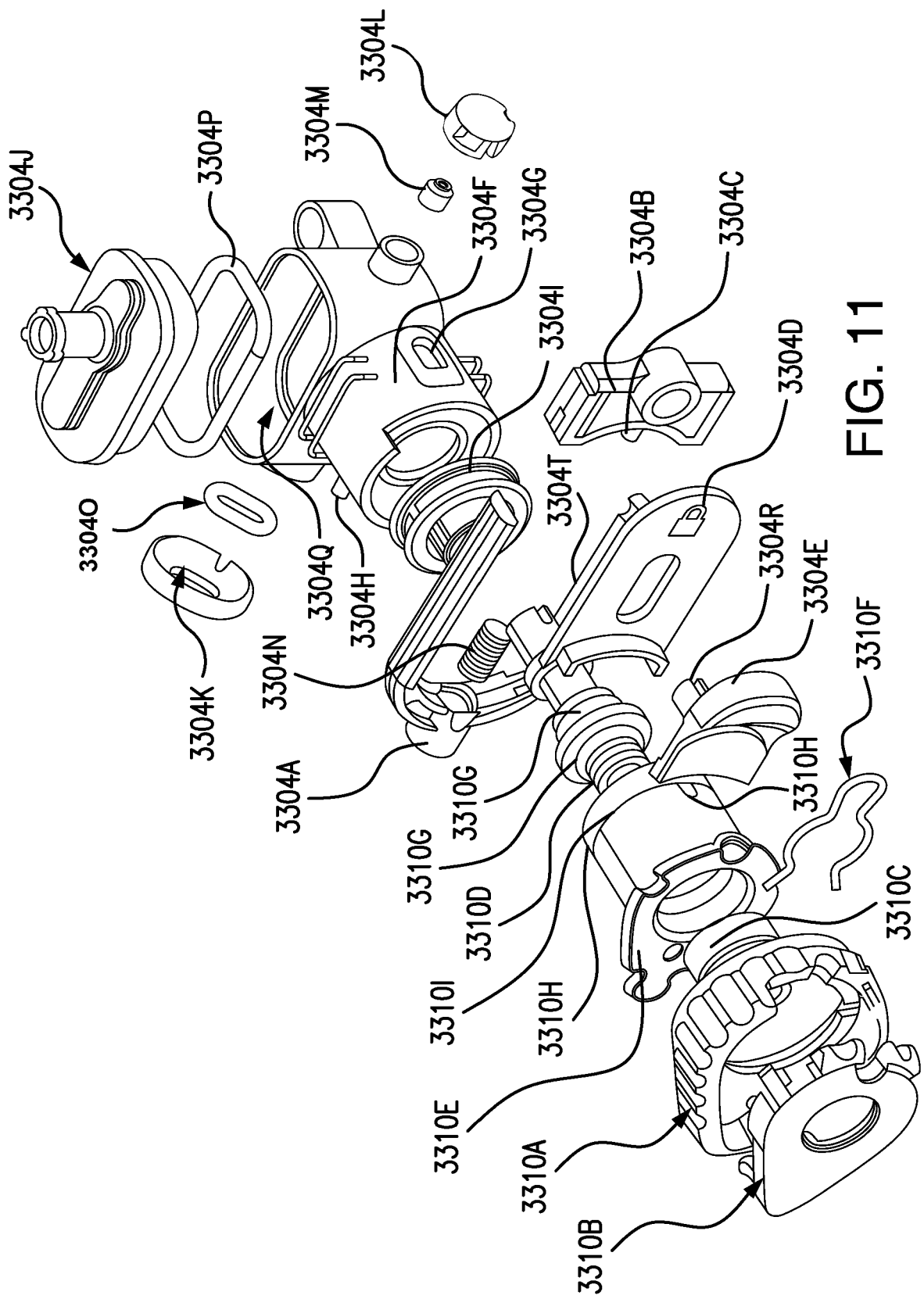
FIG. 11 is an exploded view of the lock line handle and certain features of the handle of FIG. 6.

As shown in FIGS. 9-11, for purpose of illustration and not limitation, the handle 3304 and lock line handle 3310 can include a number of elements to allow the lock line handle 3310 to operate properly, including, for example, operating the lock line 92 and releasing from the handle 3304. FIG. 10 shows a perspective view the lock line handle 3310 and related elements of the handle 3304; FIG. 11 shows an exploded view. In accordance with the disclosed subject matter, lock line handle 3310 can include lock knob 3310A, which can be gripped by a user and pivoted relative handle 3304 to operate the lock line 92 (as described in greater detail below). The lock knob 3310A can have a pear shape which can act as a flag in the unlock position to indicate to a user that the fixation device 14 is unlocked (see e.g., FIG. 15). Although shown as a pear shape, lock knob 3310A can have any suitable shape and/or configuration. Lock knob cap 3310B can be coupled to the lock knob 3310A. Screw cap 3310C can be coupled to shaft 3310D, for example via threading or other known means. Lock knob insert 3310E can be coupled lock knob shaft 3310D and lock knob 3310A. For example, a portion of the lock knob insert 3310E can be received within the lock knob 3310A. The pear shape of the lock knob 3310A and the received portion of the lock knob insert 3310E can limit relative rotation between the lock knob insert 3310E and the lock knob 3310A. Enmeshed gears of the lock knob insert 3310E and the lock knob shaft 3310D can limit relative rotation between the lock knob insert 3310E and the lock knob shaft 3310D. Furthermore, the gears can permit specific tensions or slack to be set on lock line 92. The tension needed can be different from device to device, but the gears can allow the lock knob 3310A to be aligned in a similar orientation relative the handle 3308 from device to device. As such, the lock position and the unlock position can be consistent from device to device. Rotation of the lock knob 3310A can cause rotation of the lock knob insert 3310E, and thereby cause rotation of the lock knob shaft 3310D. The lock knob insert 3310E can include a plurality of detents 3310H and a channel 3310I. Hairpin clip 3310F can be inserted between the lock knob 3310A and lock knob cap 3310B, proximate the screw cap 3310C to prevent disassembly of the lock line handle 3310 when in place, and can allow disassembly of the lock line handle 3310 when removed, for example, in case of malfunction. O-rings 3310G can be provided on the shaft 3310D. The O-rings 3310G can be any suitable O-rings, for example, –010 O-rings.

Handle 3304 can include lock knob volume 3304F, which can receive the lock knob shaft 3310D of the lock line handle 3310. Handle 3304 can include a locking system to limit movement of the lock line handle 3310 relative the handle 3304 and removal of the lock line handle 3310 relative the handle 3304. The lock system can be a latch-detent lock. For example, the latch can include a distal U-lock 3304A and a proximal U-lock 3304B coupled to one another (and collectively referred to as the "U-lock") and configured to surround lock knob volume 3304F. The proximal U-lock 3304B can include pin 3304C which can engage detents 3310H on the lock knob insert 3310E, when the pin 3304C is insert through window 3304G disposed in the lock knob volume 3304F. The distal U-lock 3304A can include a rail 3304T to engage the channel 3310I on the lock knob insert 3310E. The locking system can further include delivery catheter ("DC") handle insert 3304D and release slider 3304E, which can be used to release the lock knob 3310A. The DC handle insert 3304D can include an indication, for example, an icon (such as a lock) or writing, to indicate that the DC handle insert 3304D and the release slider 3304E are intended to lock the lock line handle 3310. For example, and not by way of limitation, release slider 3304E can include a pin 3304R that can engage the proximal U-lock 3304B (for example, through a window in DC handle insert 3304D). Spring 3304N can be supported on pin 3304H of the lock knob volume 3304F, and can bias the latch into the lock position. That is, the spring can bias the latch in a distal direction to cause the pin 3304C to engage the detents 3310H. Engagement of the pin 3304C with the detents 3310H can provide feedback, for example, audible and/or tactile, for a user that the lock knob 3310A has reached a specific position (e.g., lock, unlock, override (also referred to herein as the third position)). Pin 3304C and detents 3310H can be arranged such that the lock knob 3310A will not move from a specific position (e.g., lock, unlock, override), however, a user can move the lock knob 3310A (i.e., overcome the engagement between the pin 3304C and the detents 3310H) by turning the knob, and without touching the release slider 3304E. A portion of the distal U-lock 3304A, for example, the rail 3304T on the distal U-lock 3304A and channel 3310I can be arranged such that the lock line handle 3310 can be removed from the handle 3304 when the distal U-lock 3304A is disengaged from the channel 3310I. For example, a user can slide the release slider 3304E to disengage the distal U-lock 3304A from the channel 3310I and thereby release the lock line handle 3310. For example, sliding the release slider 3304E in the proximal direction can disengage the rail 3304T on the distal U-lock 3304A from the channel 3310I and thereby permit the user to pull the lock line handle 3310 from the handle 3308. Although a particular locking system is described, any suitable locking system can be used to limit movement of the lock knob 3304 between the lock, unlock, and override positions, and to prevent unintentional removal of the lock line handle 3310 from the handle 3304.

Lock knob volume 3304F can house the spool 33041, about which the lock line 92 can be wrapped to provide tensile load on the lock line 92. The spool 33041 can be rotationally fixed relative the lock knob shaft 3310D, for example, by a keying feature, enmeshed gears, or any suitable means. Accordingly, rotation of the lock knob 3310A, which can cause rotation of the lock knob shaft 3310D, can thereby cause rotation of the spool 33041 and therefore increase or decrease tensile load on the lock line 92 by way of the lock line 92 spooling or unspooling around the spool 33041. The lock knob volume 3304F can include a dowel pin 3304Q. The first end portion 92A of the lock line 92 can be routed around the dowel pin 3304Q and fin 3304U in the lock knob volume 3304F. This can align the first end portion 92A of the lock line 92 with the spool 33041 and can manage slack in the first end portion 92A of the lock line 92. If slack is not managed, the first end portion 92A of the lock line 92 can disengage from the spool 33041. Lock knob volume lid 3304J can close the lock knob volume 3304F, and can receive a luer fitting, or similar. O-ring retainer 3304K can have a hole through which the lock line 92 can extend. The handle 3304 can include mandrel seal retainer 3304L and mandrel seal 3304M, and O-rings, 3304O, 3304P, which can be, for example, a −009 O-ring and a −020 O-ring, respectively. Although a specific arrangement for loading and unloading the lock line 92 is provided, any suitable means of loading and unloading the lock line 92 can be used.

Figure 13B:
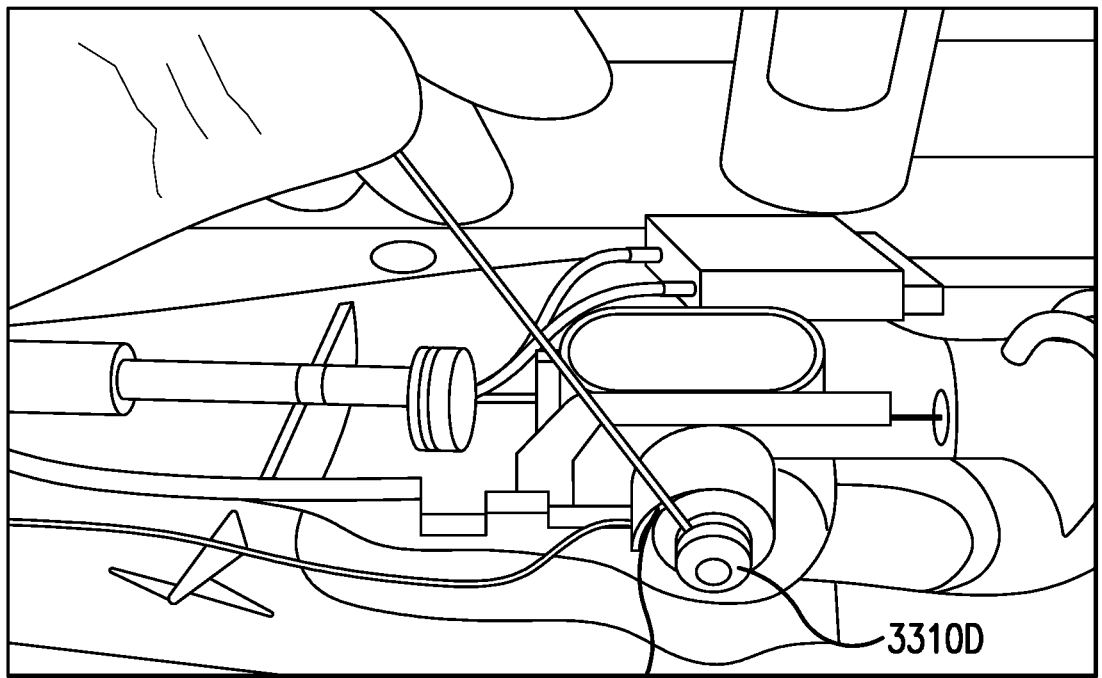
FIGS. 13B and 13C are perspective views of certain features of a lock line handle and handle, in accordance with the disclosed subject matter.
Figure 13C:
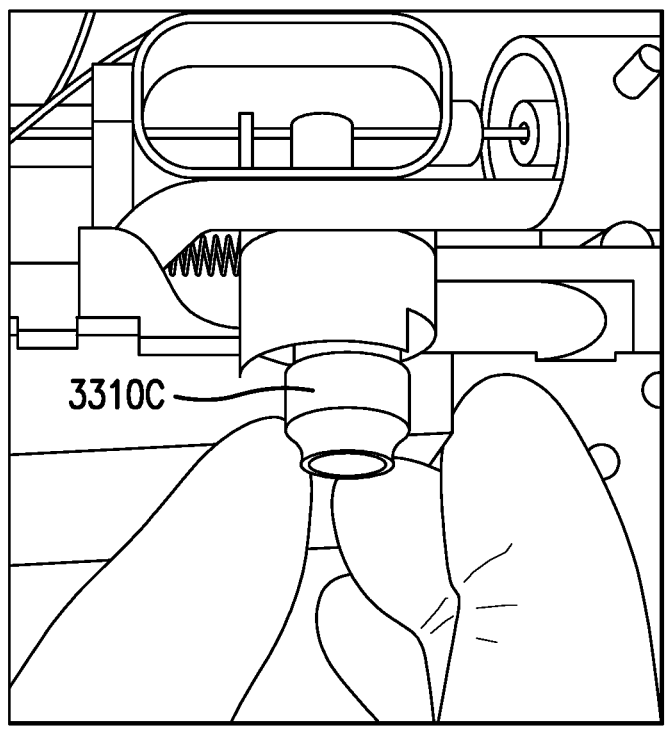

As shown in FIGS. 12 and 13A-13C, for purpose of illustration and not limitation, the first end portion 92A and the second end portion 92B of the lock line 92 can extend through O-ring retainer 3304K. As noted above, the first end portion 92A can be routed around the dowel pin 3304Q and relative fin 3304U, and routed around spool 33041. The first end portion 92A can further extend within the lock knob shaft 3310D and can be fixedly coupled to the lock line handle 3310, for example, by screw cap 3310C. For example, the first end portion 92A can extend through the lock knob shaft 3310D and then be wrapped around lock knob shaft 3310D (FIG. 13B). The screw cap 3310C can be coupled to the lock knob shaft 3310D (FIG. 13C) to fixedly couple the first end portion 92A to the lock line handle 3310. The second end portion 92B can be releasably coupled to the lock line handle 3310. For example, second end portion 92B can extend into the spool 33041 and between the spool 33041 and lock knob shaft 3310D to trap ("sandwich") the second end portion 92B therebetween. Accordingly, when the lock line handle 3310 is coupled with the handle 3304, the second end portion 92B can be releasably coupled to the lock line handle 3310, and when the lock line handle 3310 is decoupled (released) from the handle 3304, the second end portion 92B can be decoupled (released) from the lock line handle 3310. Although, described with specific arrangements for fixedly and releasably coupling the first end portion 92A and second end portion 92B of the lock line 92, respectively, any suitable arraignments for fixedly and releasably coupling the respective end portions can be used.

The system can be flushed via a port in a fluid management system 3326 (FIG. 9). For example, flush fluid can enter the lock knob volume 3304F from the distal end through the O-ring retainer 3304K. During preparation of the device, air can exit the device through a luer port in the lock knob volume lid 3304J. When de-airing is complete, a cap 3304S can be placed on the luer port. The cap 3304S can be a red cap 3304S, which can be easily noticed by a user, however, any suitable cap shape and/or color can be used. As noted, O-rings (e.g., 3304P, 3304O) and mandrel seal 3304M can keep hemostasis throughout the procedure. Although fluid flushing and de-airing is described in a particular arrangement, any suitable arrangement can be used for flushing and de-airing.

Figure 14:
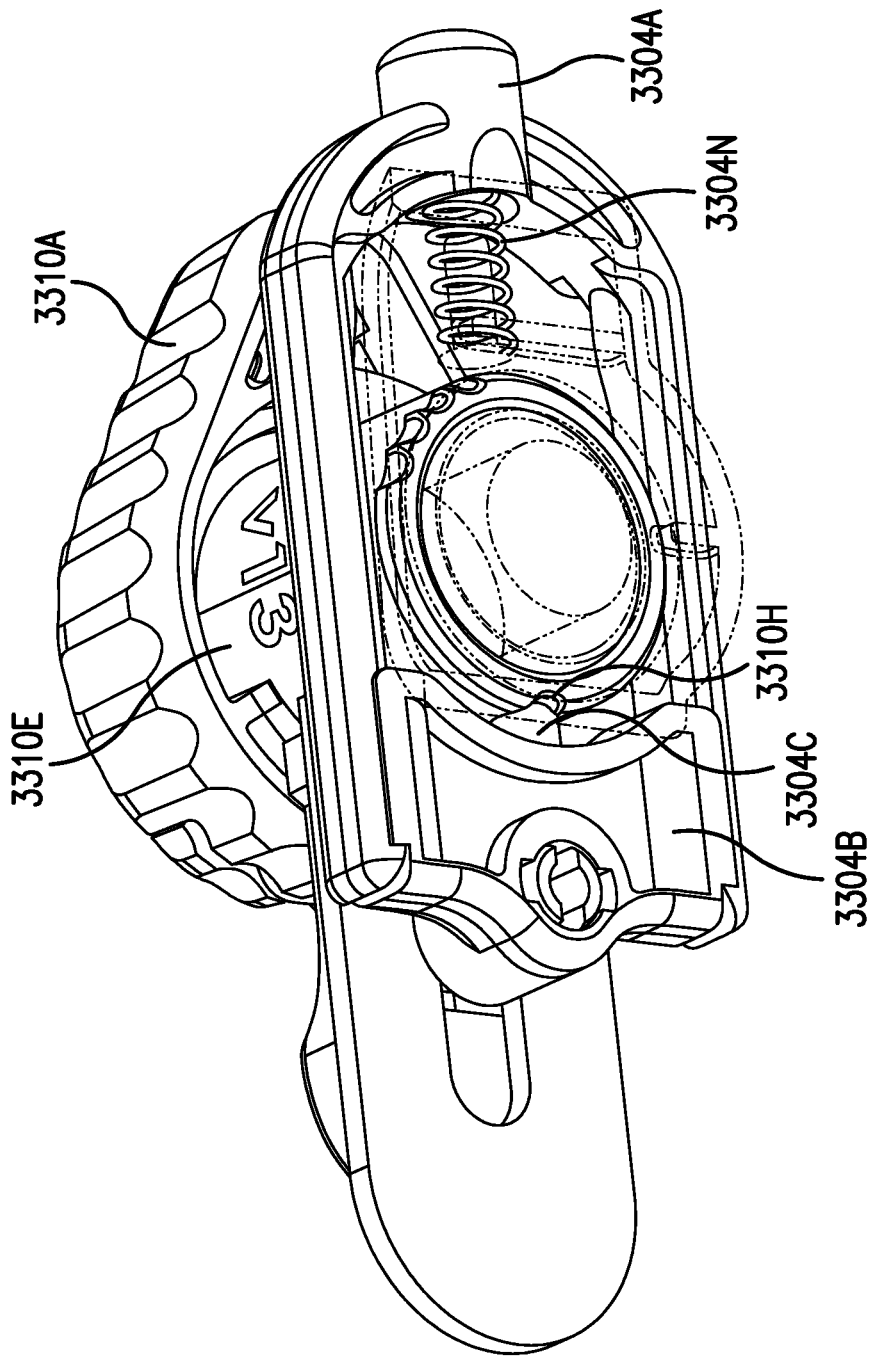
FIG. 14 is a perspective view of the lock line handle in the lock position and certain features of the handle of FIG. 6.

In operation, the fixation device 14 can be delivered in a lock position (as described above). The lock knob 3310A can be in the lock position, which is shown for example, in FIGS. 8 and 14. In the lock position, the lock line 92 can have no (or relatively low) tension and the lock knob 3310A can point distally. Spring 3304N can bias distal U-lock 3304A and proximal U-lock 3304B in a distal direction and therefore bias pin 3304C to engage detent 3310H of the lock knob insert 3310E (FIG. 14). Although described in a particular arrangement, the lock position can include any suitable arrangement.

Figure 15:
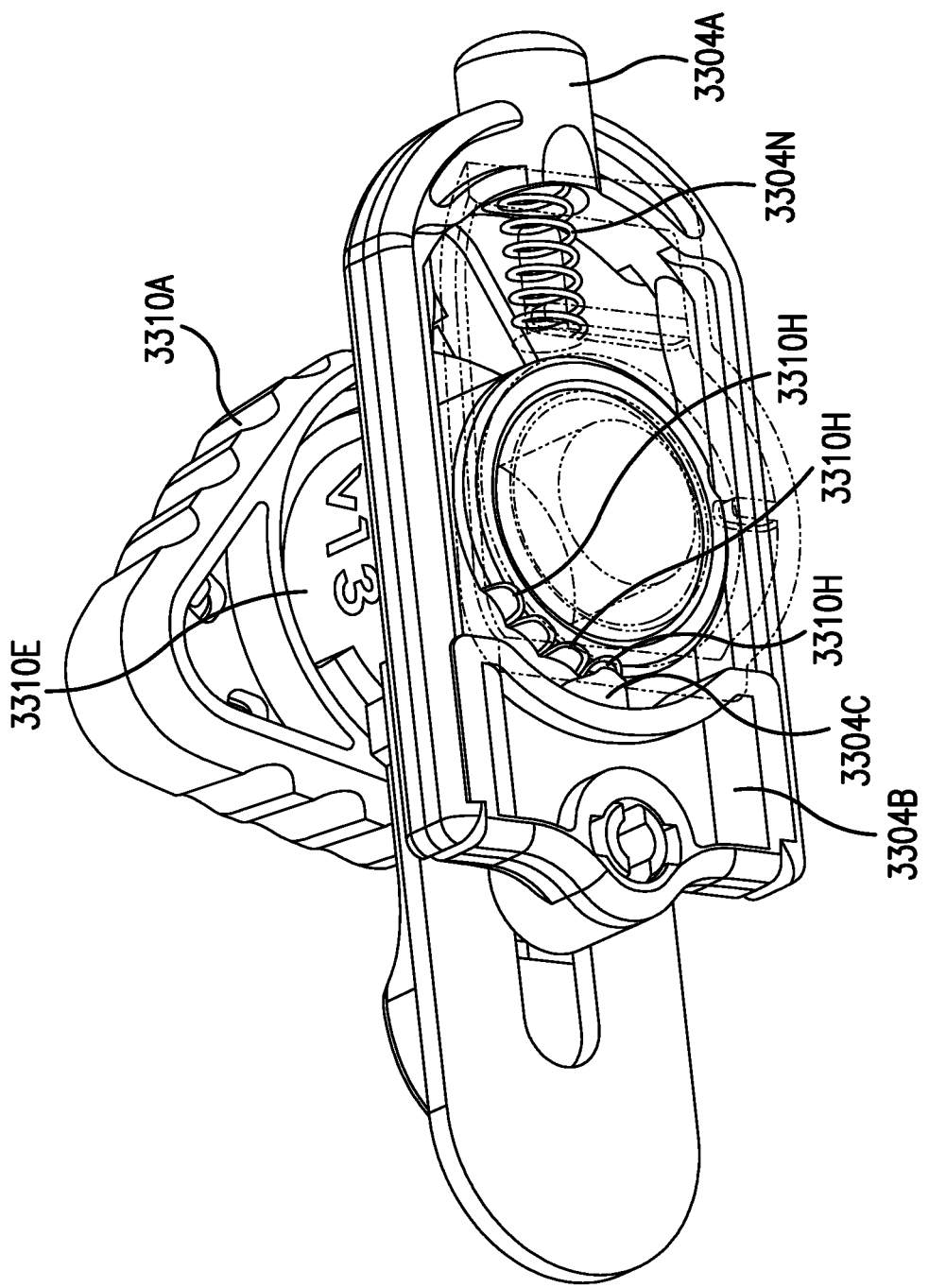
FIG. 15 is a perspective view of the lock line handle in the unlock position and certain features of the handle of FIG. 6.
Figure 16:
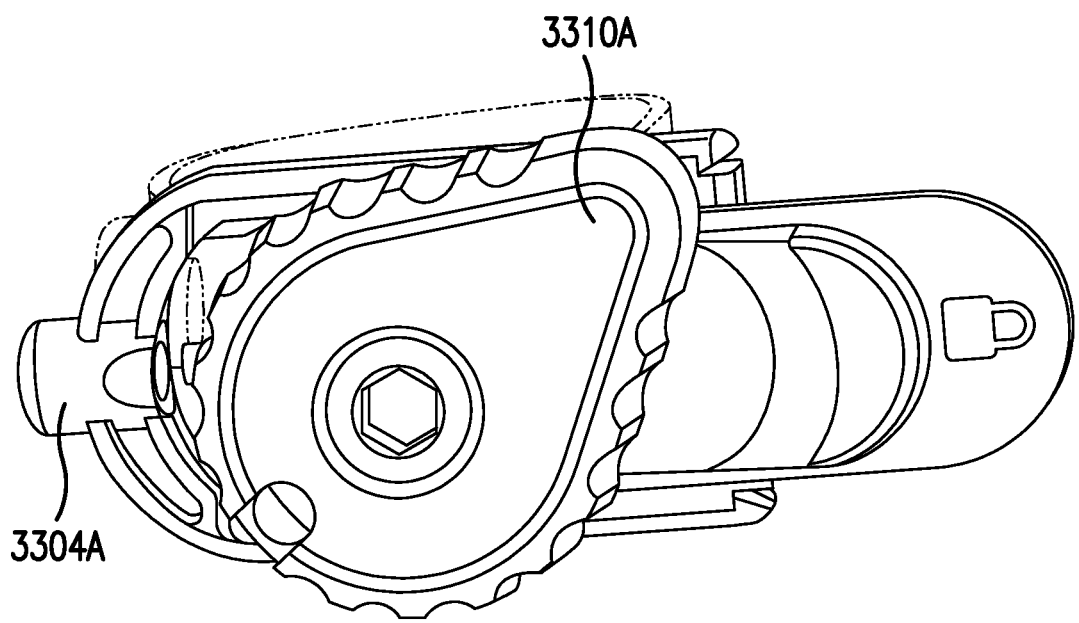
FIG. 16 is a perspective view of the lock line handle in the third position and certain features of the handle of FIG. 6.
Figure 17A:
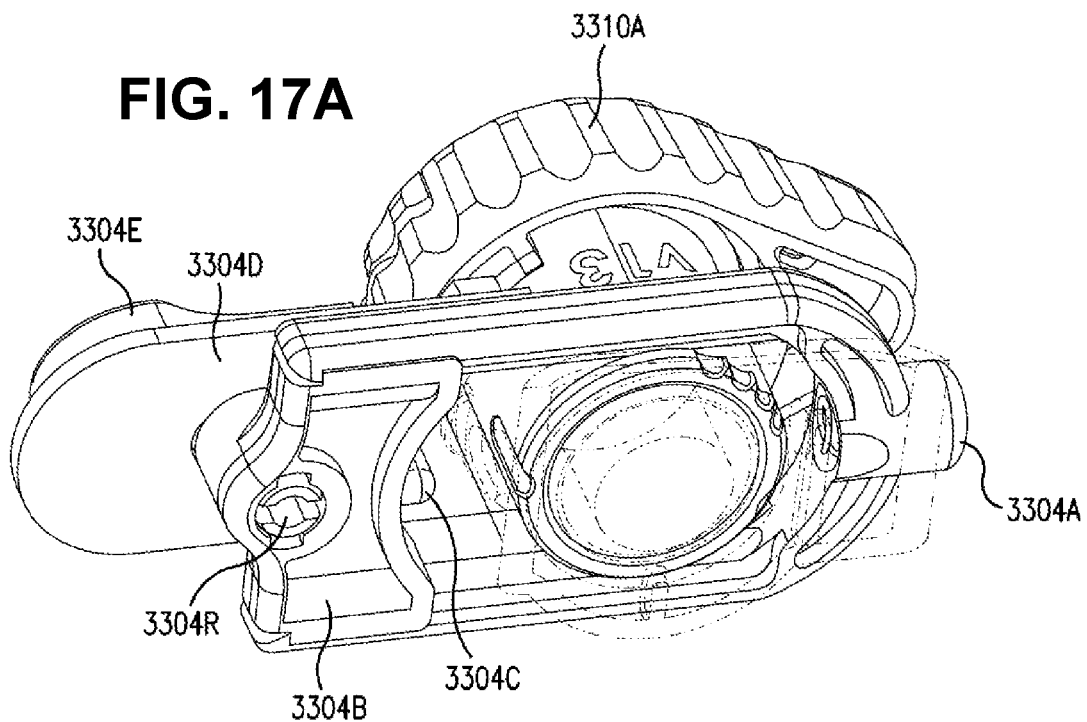
FIGS. 17A and 17B are perspective views of the lock line handle and certain features of the handle of FIG. 6, including the release slider pulled to a proximal position.
Figure 17B:
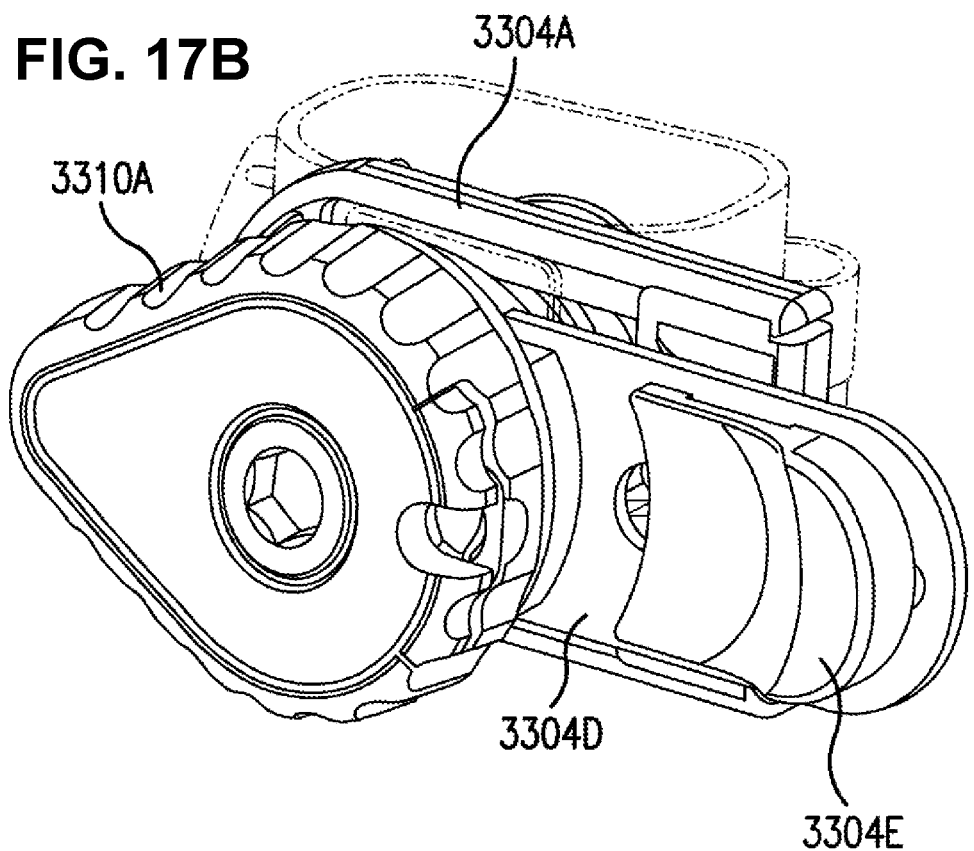

During a procedure, the user can turn the lock knob 3310A to the unlock position to apply tension (or relatively higher tension) to the lock line 92. Turning the lock knob 3310A can overcome the engagement of the pin 3304C with detent 3310H. For example, the lock knob 3310A can be rotated in a clockwise rotation (as viewed in FIG. 8) such that the lock knob 3310A can point upwardly (FIG. 15). In such a position, the lock knob 3310A itself can indicate to the user that the fixation device 14 is in the unlock position. Rotating the lock knob 3310A can cause spool 33041 to rotate (as described above) and can increase tension on the lock line 92 as the lock line 92 spools around the spool 33041. As noted above, increasing tension on lock line 92 can apply a force on harness 108 which can unlock the fixation device 14, as described above. Spring 3304N can bias distal U-lock 3304A and proximal U-lock 3304B in a distal direction and therefore bias pin 3304C to engage detent 3310H of the lock knob insert 3310E (FIG. 15) and bias the rail 3304T on the distal U-lock 3304A to engage the channel 3310I of the lock knob insert 3310E. The detents 3310H (as well as labeling) can define the lock and unlock positions. A click sound can be made as the pin 3304C engages detent 3310H. The detent 3310H can also prevent the lock knob 3310A from returning to the lock position (until a user engages the lock knob 3310A). Although described in a particular arrangement, the unlock position can include any suitable arrangement. The user can lock the fixation device 14 by rotating the lock knob 3310A in the counterclockwise direction (as viewed in FIG. 8) to return the lock knob to the lock position, unspool the lock line 92 from spool 33041, and decrease tension on lock line 92. A click sound can be made as the pin 3304C engages detent 3310H. The rail 3304T can remain engaged with the channel 3310H even as the handle moves between the lock, unlock, and third position. Although a particular method of operating the lock line handle is described, and suitable method of operating the lock line handle can be used to increase or decrease tension on lock line 92.

The lock knob 3310A can be rotated beyond the unlock position (see e.g., FIG. 16), to a third position, and to thereby further increase tension on the lock line 92. This can be useful during certain procedures to ensure that the fixation device 14 properly locks. Additional detents 3310H can be provided to engage the pin 3304C and hold the lock knob 3310A in the third position or further rotated positions. The rail 3304T can remain engaged with the channel 3310H even as the handle moves between the lock, unlock, and third positions. Although described in a particular arrangement, the third position, and any further positions, can include any suitable arrangement.

Figure 18:
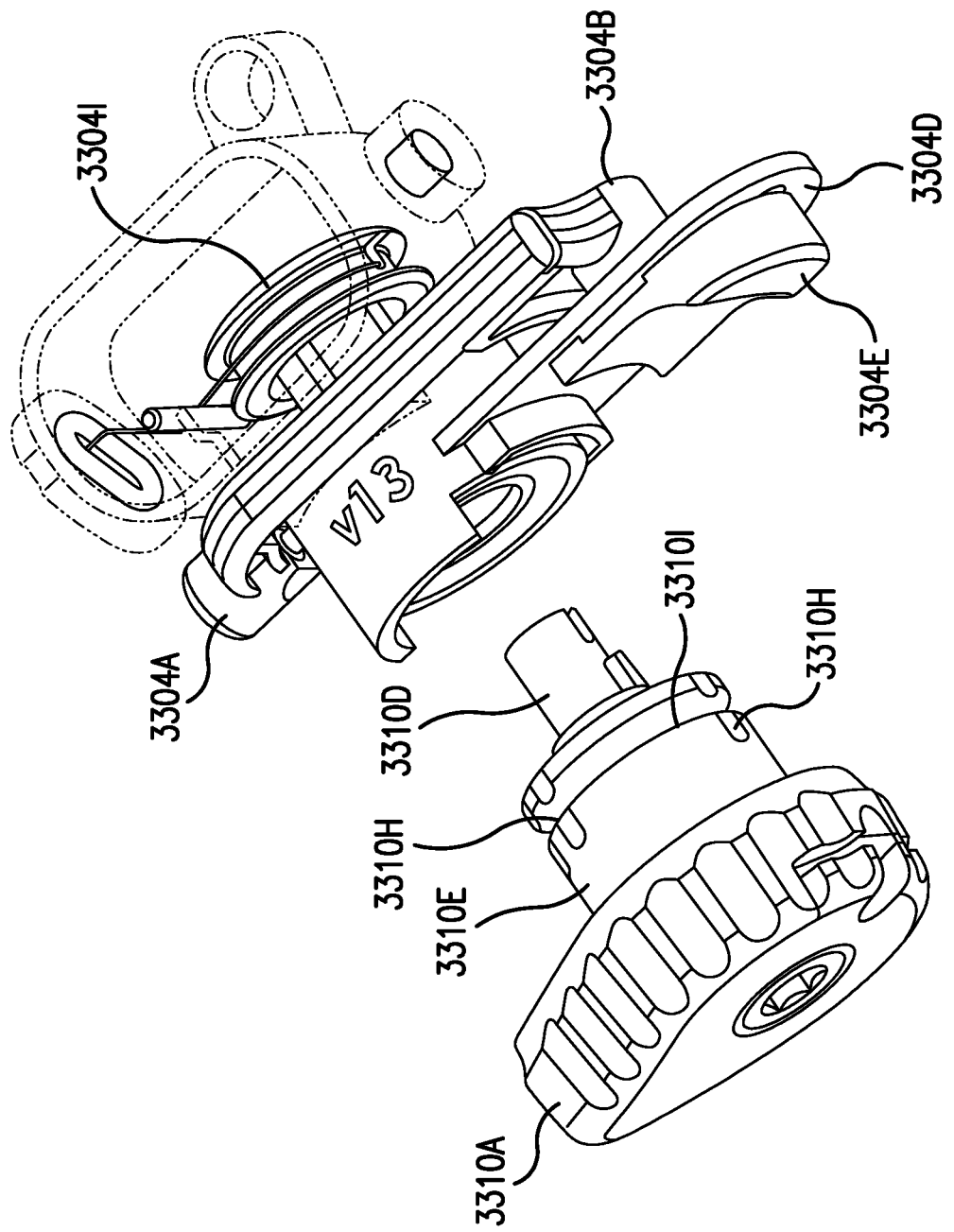
FIG. 18 is a perspective view of the lock line handle and certain features of the handle of FIG. 6, with the lock line handle removed.

Before the fixation device 14 can be deployed from the delivery device 300, the lock line 92 must be decoupled from the fixation device 14. To remove the lock line 92, the user can ensure that the lock knob 3310A is in the lock position. The user can retract the release slider 3304E (i.e., the release slider can be pulled in the proximal direction). This can pull the proximal U-lock 3304B (for example via pin 3304R) and the distal U-lock 3304A in a proximal direction (FIGS. 17A and 17B), which can disengage the rail 3304T of the distal U-lock 3304A from channel 3310I. The user can pull the lock line handle 3310 off the handle 3304 (FIG. 18). Withdrawing the lock line handle 3310 can release the second end portion 92B of lock line 92 from between the spool 33041 and lock knob shaft 3310D, while the first end portion 92A remains fixed to the lock line handle 3310. Accordingly, withdrawing the lock line handle 3310 pulls one end portion of the lock line 92 (i.e., first end portion 92A), while the other end portion (i.e., the second end portion 92B) is free to travel distally along the length of the shaft 302, through the fixation device 14, and proximally along the length of the shaft 302. Therefore, pulling the lock line handle 3310 away from the handle 3304 with withdraw the lock line from the delivery system 300 and fixation device 14.

Figure 19:
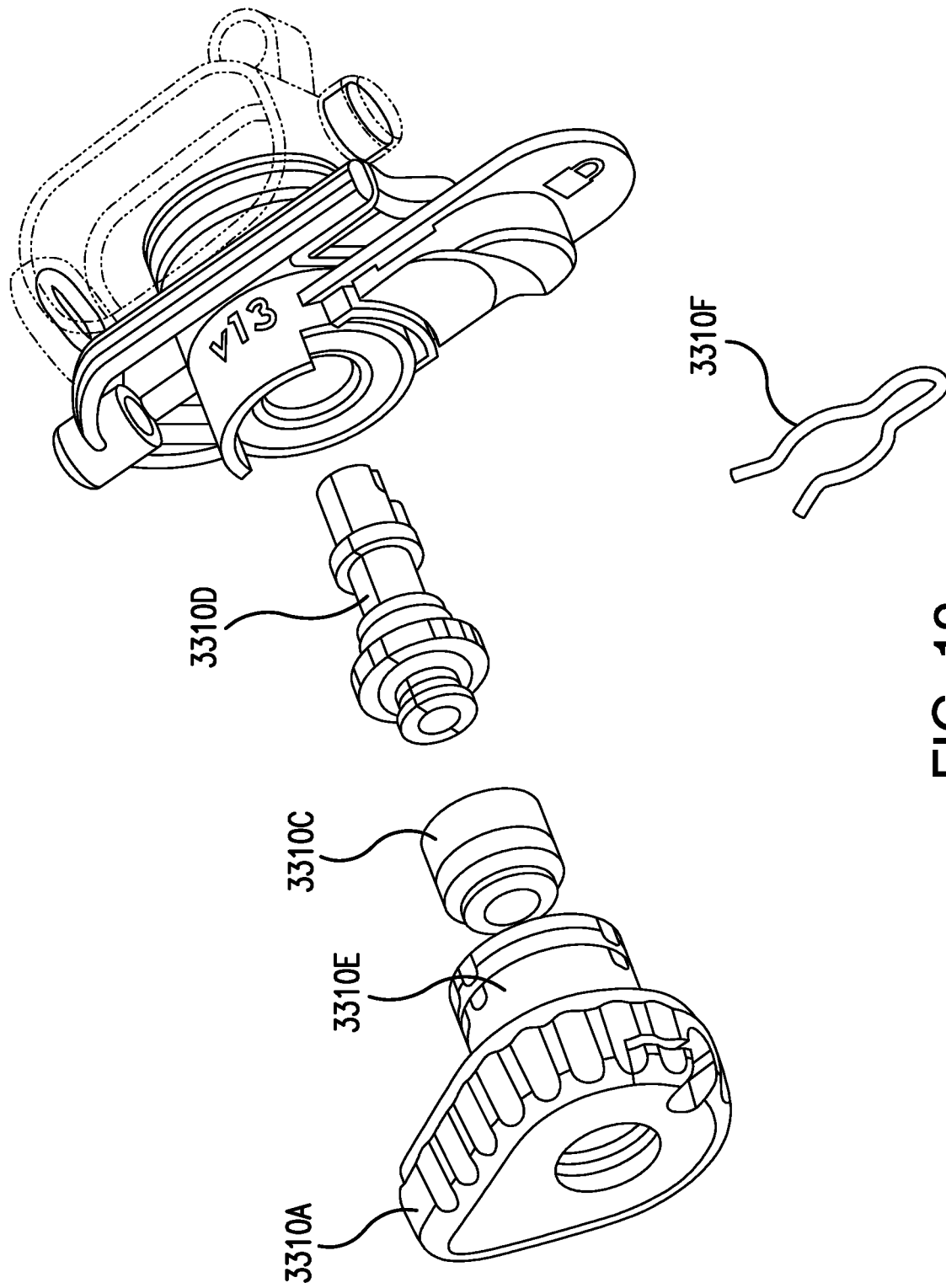
FIG. 19 is a perspective view of a disassembled lock line handle and certain features of the handle of FIG. 6.

If the first end portion 92A of the lock line 92 becomes stuck, the user can disassemble the lock line handle 3310 (FIG. 19). For example, the user can remove hairpin clip 3310F and remove the lock knob 3310A and lock knob insert 3310E from the lock knob shaft 3310D. The user can then unscrew screw cap 3310C from the lock knob shaft 3310D. This can provide access the first end portion 92A. The user can pull the second end portion 92B of the lock line 92 to pull to free the "stuck" first end portion 92A. Although a particular method of disassembling the handle is described, any suitable method for disassembling the handle can be used.

Figure 20:
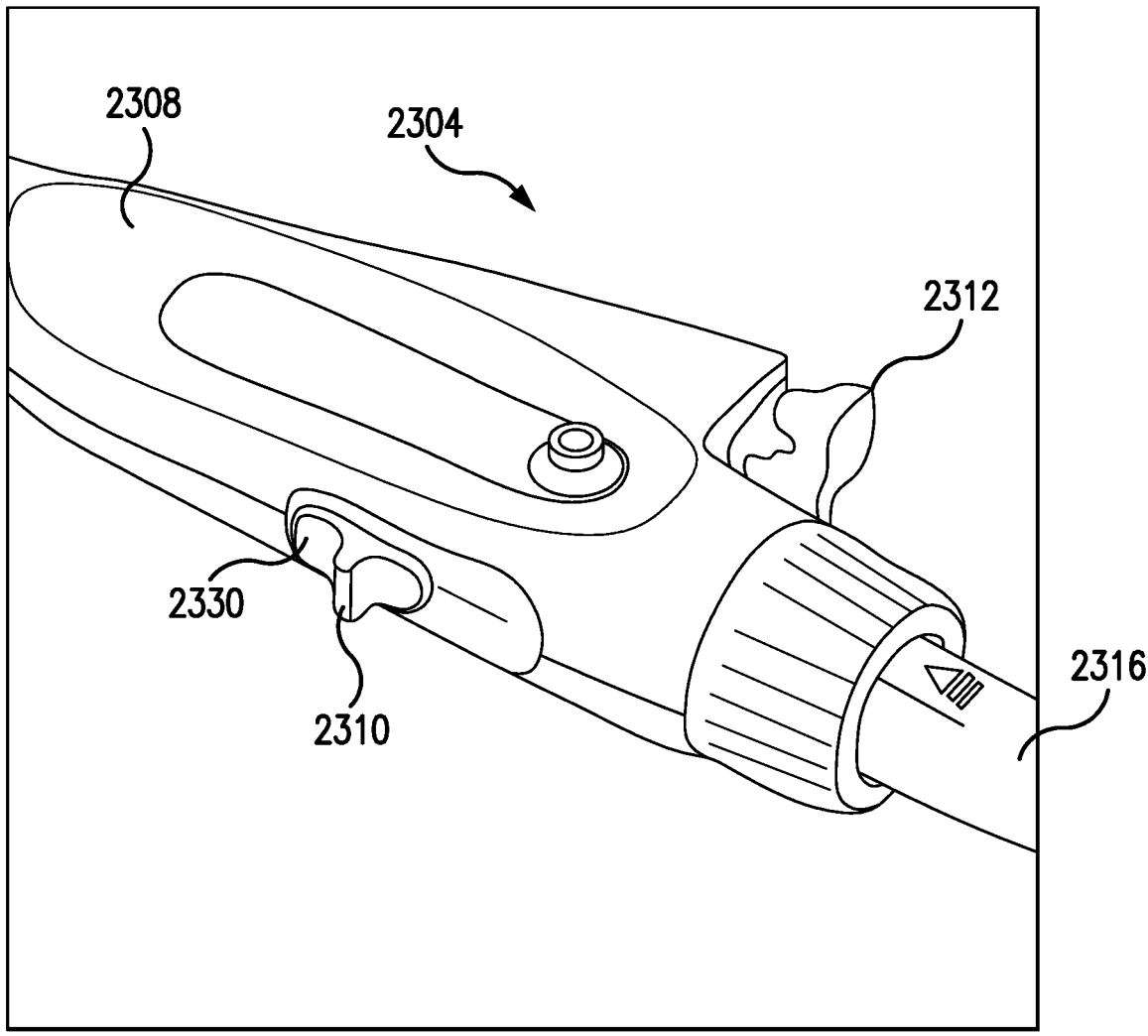
FIG. 20 is a perspective view of a handle, including a slider lock line handle, in accordance with the disclosed subject matter.
Figure 21A:
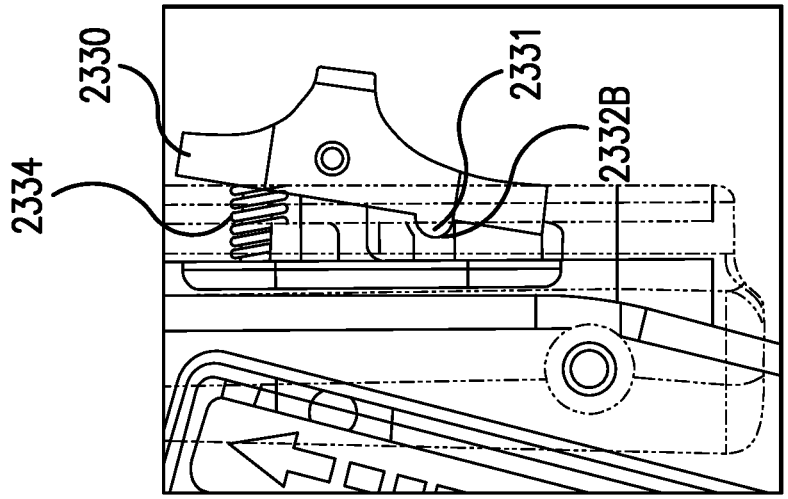
FIGS. 21A-C are enlarged detail views of the slider lock line handle of FIG. 20.
Figure 21B:
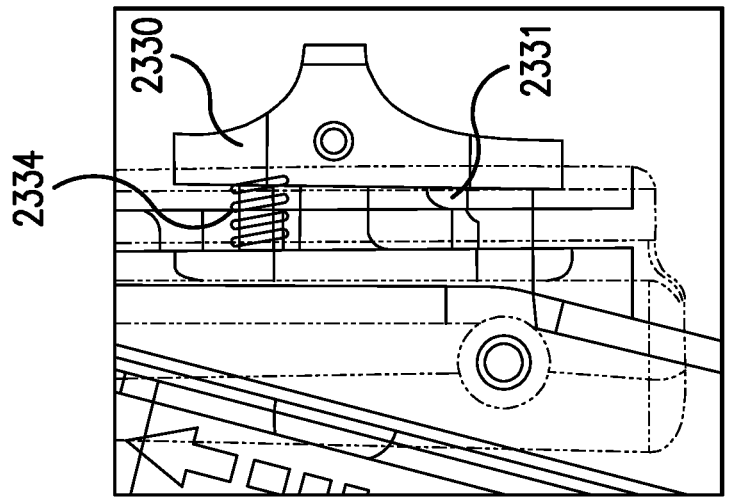
Figure 21C:
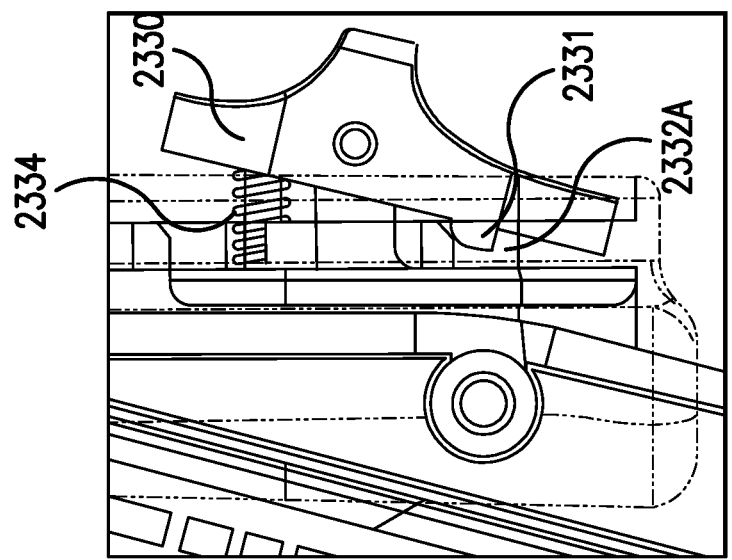

In accordance with the disclosed subject matter, a variety of lock line handle designs can be used to operate, release, and retract the lock line 92. For example, and with reference to FIG. 20-21C for purpose of illustration and not limitation, handle 2304 can have any of the features described herein above related to handles. For example, handle 2304 can include main body 2308, lock line handle 2310, gripping element line handle 2312, and actuator rod handle 2316. Lock line handle 2310 can include slider 2330, which can be, for example, a thumb slide. Lock line 92 (not shown) can extend from slider 2330 to the harness 108 of fixation device 14. The slider 2330 can be moveable between a lock (e.g., forward, distal) position (FIG. 21A) and an unlock (e.g., retracted, proximal) position (FIG. 21C). Slider 2330 can be slidable between the lock and unlock positions (FIG. 21B). Moving slider 2330 from the lock position toward the unlock position can increase tension on the lock line 92, and therefore apply a force on harness 108 which unlocks the fixation device 14, as described above. Moving slider 2330 from the unlock position toward the lock position can reduce tension on the lock line 92, and therefore reduce the force on harness 108 which locks the fixation device 14, as described above. Slider 2330 can include a lock assembly, for example, a latch-detent lock, to audibly and/or tactically indicate to the user that the slider 2330 has reached the lock or unlock position. For example, slider 2330 can include latch 2331, which can be received in detent 2332A in the lock position and detent 2332B in the unlock position. Spring 2334 can ensure that latch 2331 engages detents 2332A, 2332B as slider 2330 slides relative the lock and unlock positions. Slider 2330 can include an ergonomic shape for receiving a user's thumb or finger to push slider 2330 and release latch 2331 from detents 2332A, 2332B. Additionally, slider 2330 can include an override mechanism to selectively prevent actuation of the slider 2330 from the unlock position to a third position. Actuating the slider 2330 from the unlock position to the third position can increase tension on the lock line 92 beyond the tension on the lock line 92 when the lock line handle 2310 is in the unlock position. This third position can be useful during troubleshooting. The override mechanism can be a latch-detent lock, pin, push button, slide or the like.

Referring to FIGS. 22A-22C, for purpose of illustration and not limitation, slider 2330 can be releasably coupled to the main body 2308. The lock line 92 can include a first portion fixedly coupled to the slider 2330 and a second portion releasably coupled to the slider 2330. The lock line 92 can further have an intermediate portion that extends to and is releasably coupled to the harness 108 of fixation device 14 disposed proximate the distal end of the shaft 302. Accordingly, to release the harness 108, the second portion of lock line 92 can be released from the slider 2330, and the slider 2330 can be released and pulled away from handle 304, thereby withdrawing the lock line 92. As shown in FIG. 22A, slider 2330A slides away from handle 304 to deploy. Slider 2330A can include release assembly 2340A to prevent unwanted release. Release assembly 2340A can include, for example, a slide 2342A and catch 2341A. As shown in FIG. 22B, slider 2330B rotates off handle 304 to deploy. Slider 2330B can include release assembly 2340B to prevent unwanted release. Release assembly 2340B can include, for example, a catch 2341B. As shown in FIG. 22C, slider 2330C is released by pinch button release assembly 2340C. Pinch button release assembly 2340 can move catch 2341C and thereby release slider 2330C. The process of releasing the slider 2330 (e.g., 2330A, 2330B, 2330C) can simultaneously release the second portion of the lock line 92. The slider 2330 (e.g., 2330A, 2330B, 2330C) can then be withdrawn, and can likewise withdraw lock line 92 because the first portion remains coupled to the slider 2330 (e.g., 2330A, 2330B, 2330C).

Figure 23:
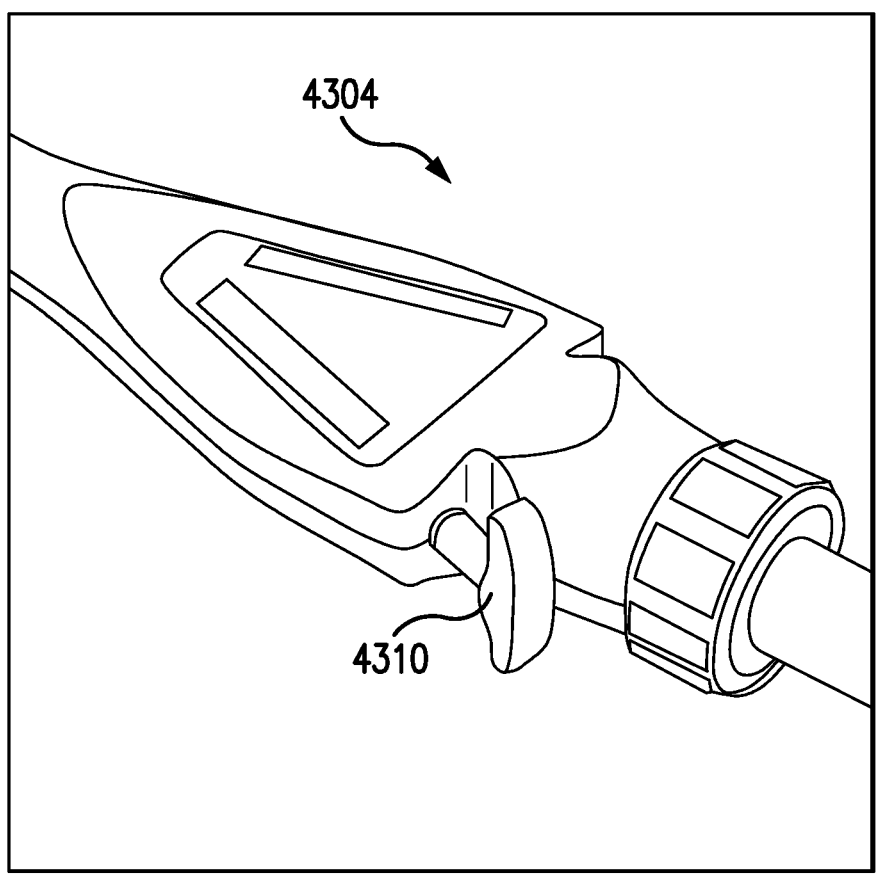
FIG. 23 is a perspective view of handle, including a T-shape lock line handle, in accordance with the disclosed subject matter.
Figure 24:
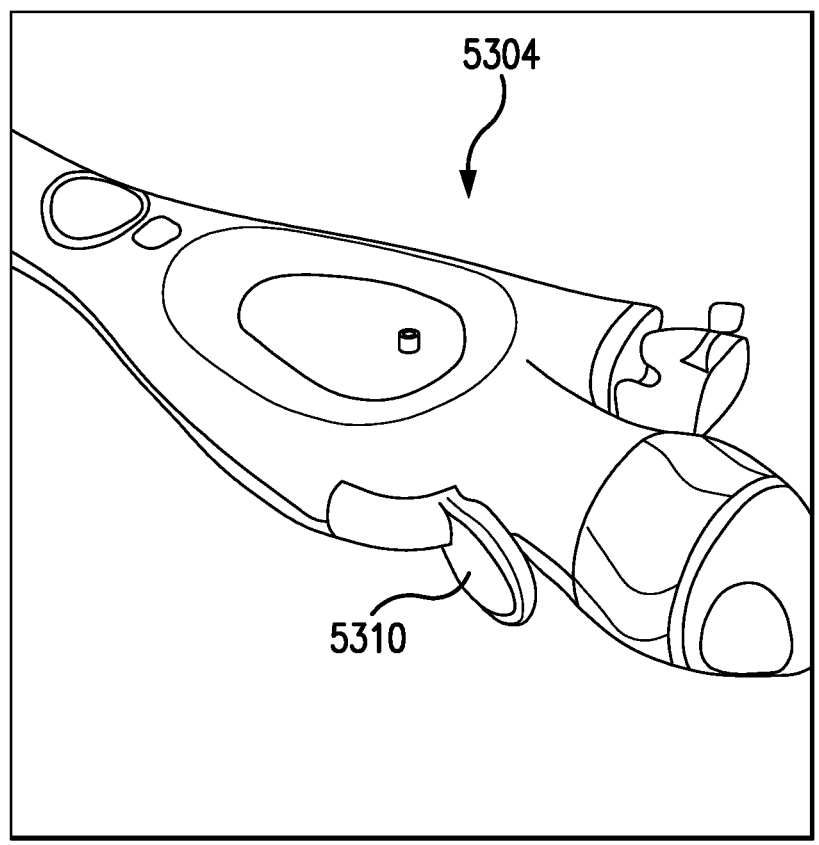
FIG. 24 is a perspective view of a handle, including a pivotable lock line handle, in accordance with the disclosed subject matter.
Figure 25A:
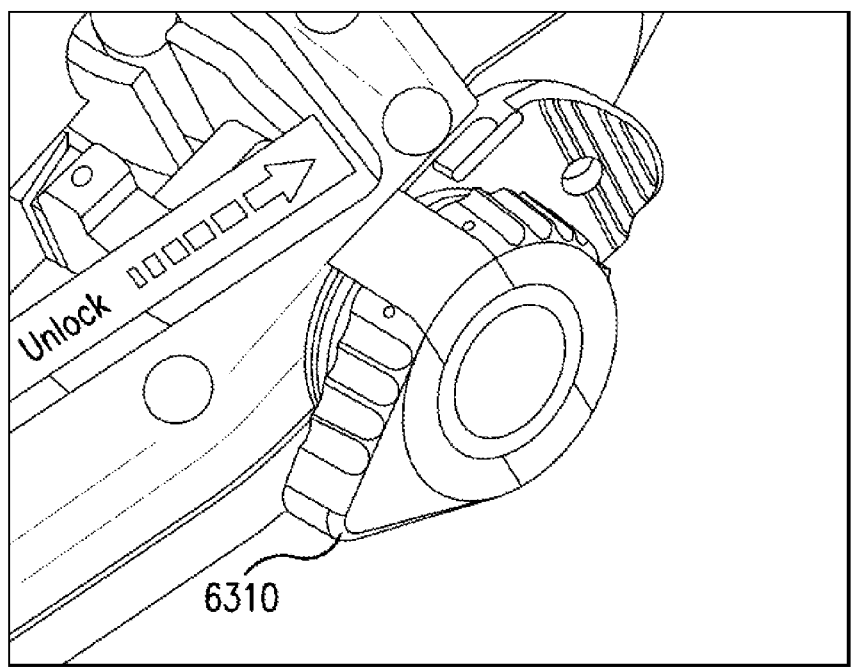
FIG. 25A is a perspective view of a pivotable lock line handle in the lock position, in accordance with the disclosed subject matter.
Figure 25B:
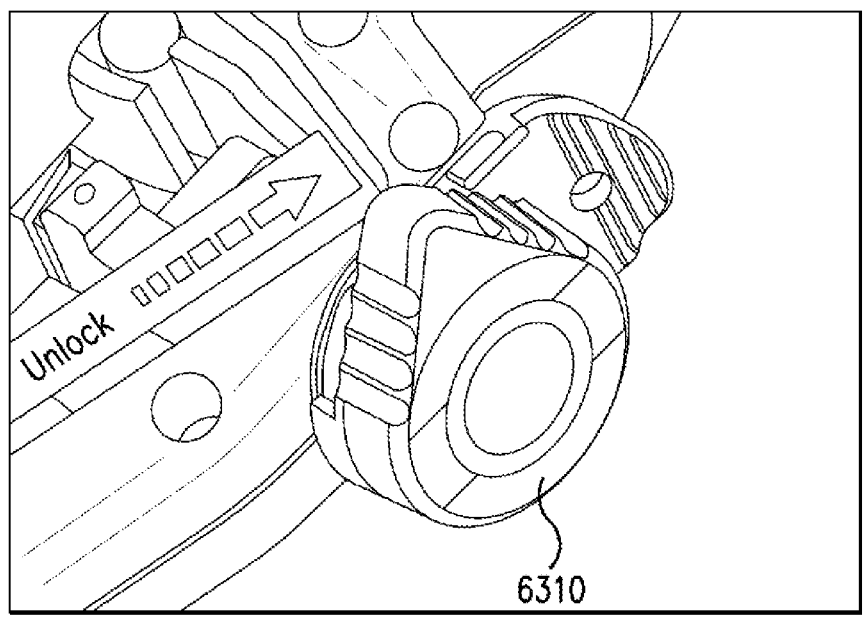
FIG. 25B is a perspective view of the pivotable lock line handle of FIG. 25A in the unlock position.
Figure 26A:
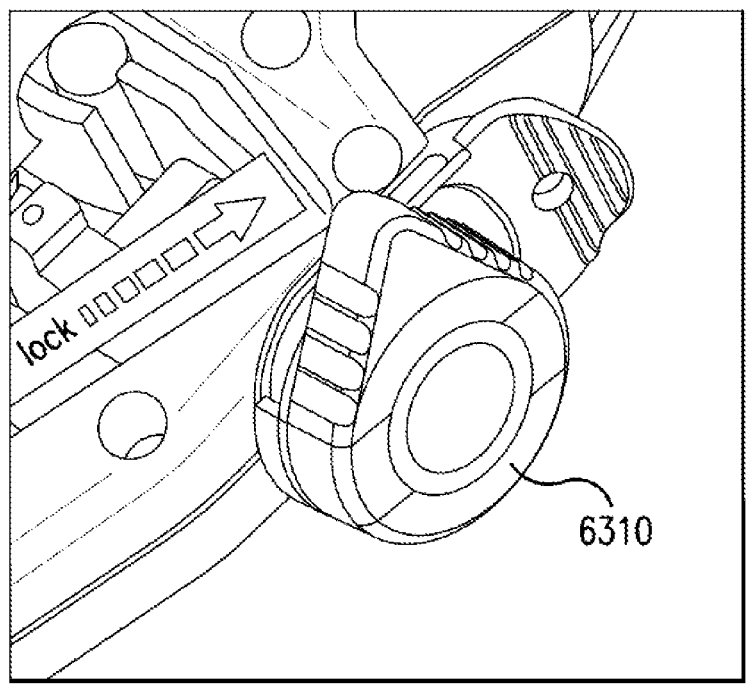
FIGS. 26A-B are perspective views of the lock line handle of FIG. 25A in the unlock position and third position, respectively.
Figure 26B:
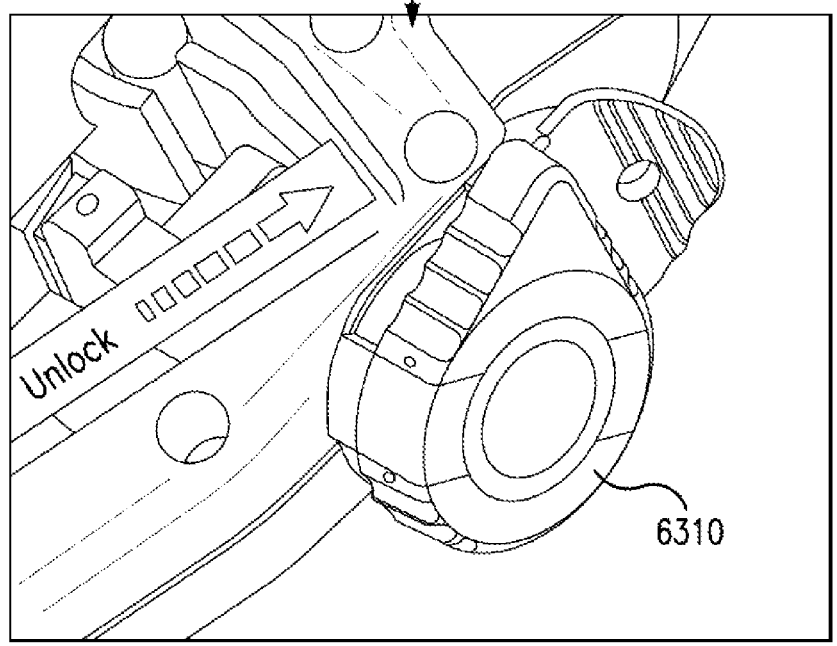

Although particular lock line handles are described herein, this disclosure contemplates any suitable lock line handle. For example, and with reference to FIG. 23 for purpose of illustration and not limitation, handle 4304 can have any of the features described herein above related to handles. For example, handle 4304 can include the lock line handle 4310. Lock line handle 4310 can have a T-shape, or similar shape for ergonomic grasping. Although shown as a T-shape, any ergonomic shape which can allow a user to easily apply a significant amount of proximal force on handle 4310 is suitable. Lock line handle 4310 can be in a distal position (FIG. 23) to lock the fixation device 16, and lock line handle 4310 can slide relative handle 4304, for example, proximally, to lock the fixation device. With reference to FIG. 24 for purpose of illustration and not limitation, handle 5304 can have any of the features described herein above related to handles. For example, lock line handle 5314 can be configured to pivot relative the handle to actuate between the lock position and the unlock position. For example, lock line handle can be in a distal position (not shown) to lock the fixation device 16 and can rotated relative handle 5304 to a proximal position to unlock the fixation device 16 (FIG. 24). Referring to FIGS. 25A-26B for purpose of illustration and not limitation, handle 6304 can have any of the features described herein above related to handles. Lock line handle 6310 can have a pear shape, as described above. FIGS. 25A and 25B show the lock line handle 6310 in the lock position and unlock position, respectively. As noted above, the lock line handle can act as a flag in the unlock position to indicate to a user that the fixation device 14 is unlocked. FIGS. 26A and 26B show the lock line handle in the unlock position and the third position, respectively.

Figure 27A:
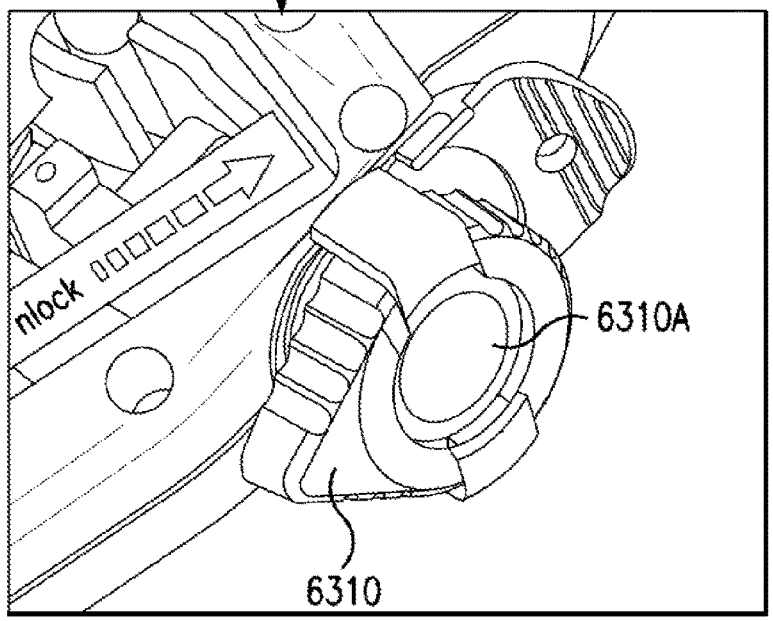
FIGS. 27A-B are perspective views of the lock line handle of FIG. 25A being released from the handle.
Figure 27B:
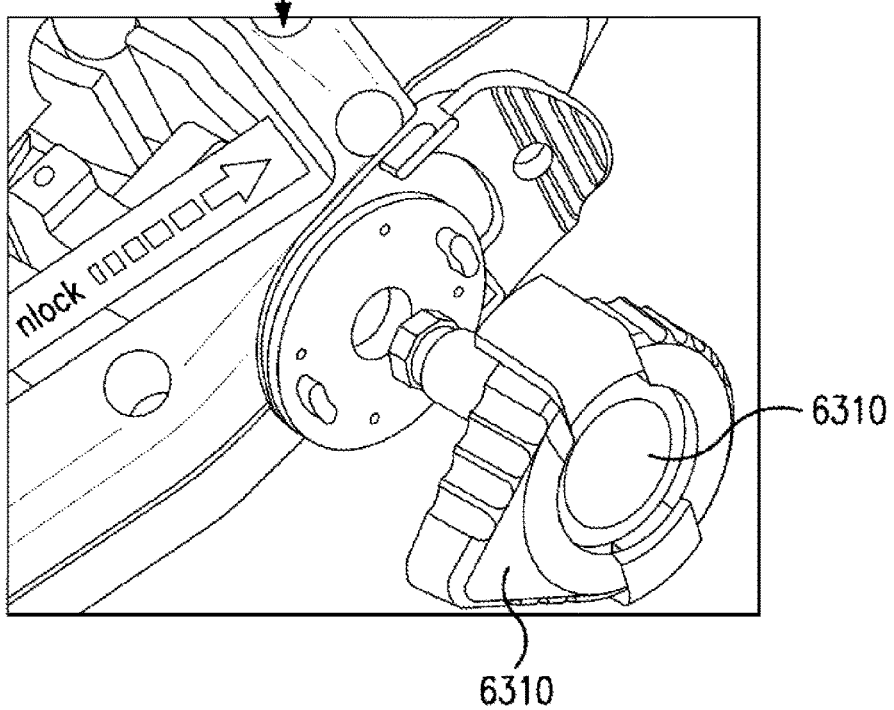
Figure 28B:
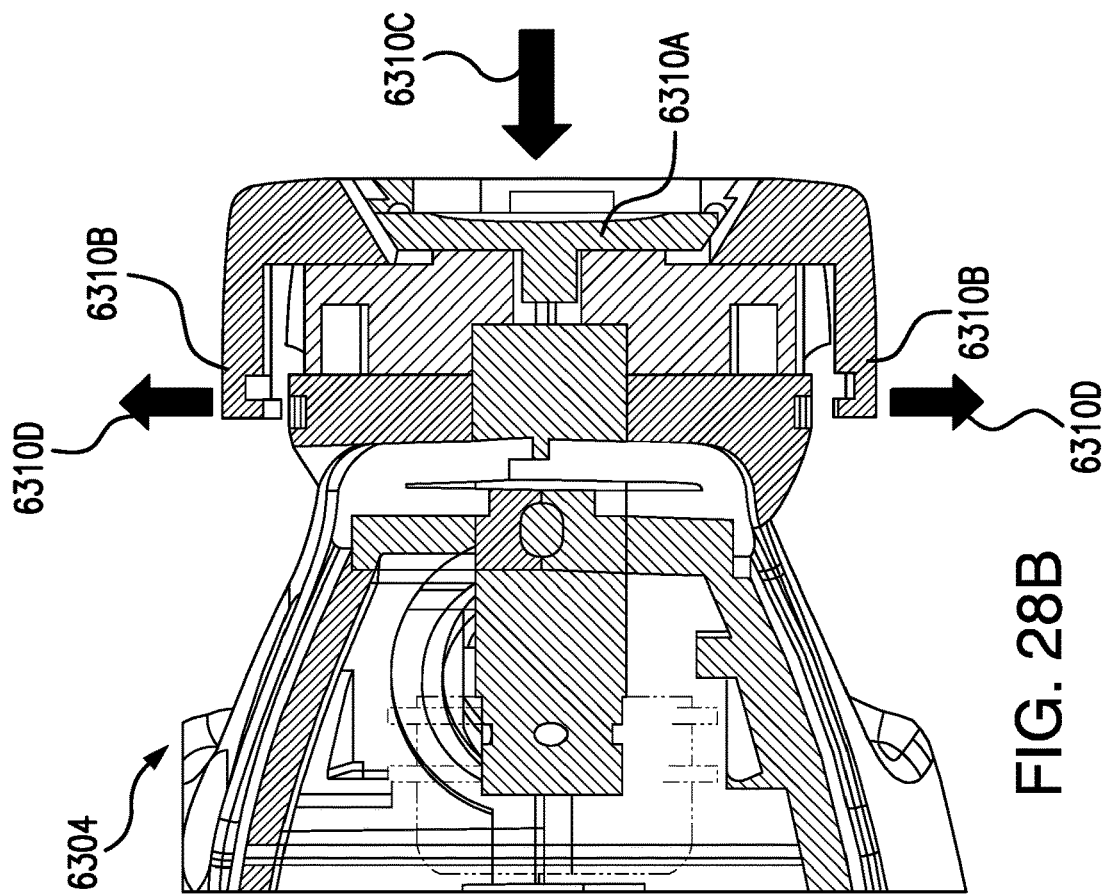
FIGS. 28A-B are cut-away views of the lock line handle of FIG. 25A.
Figure 28A:
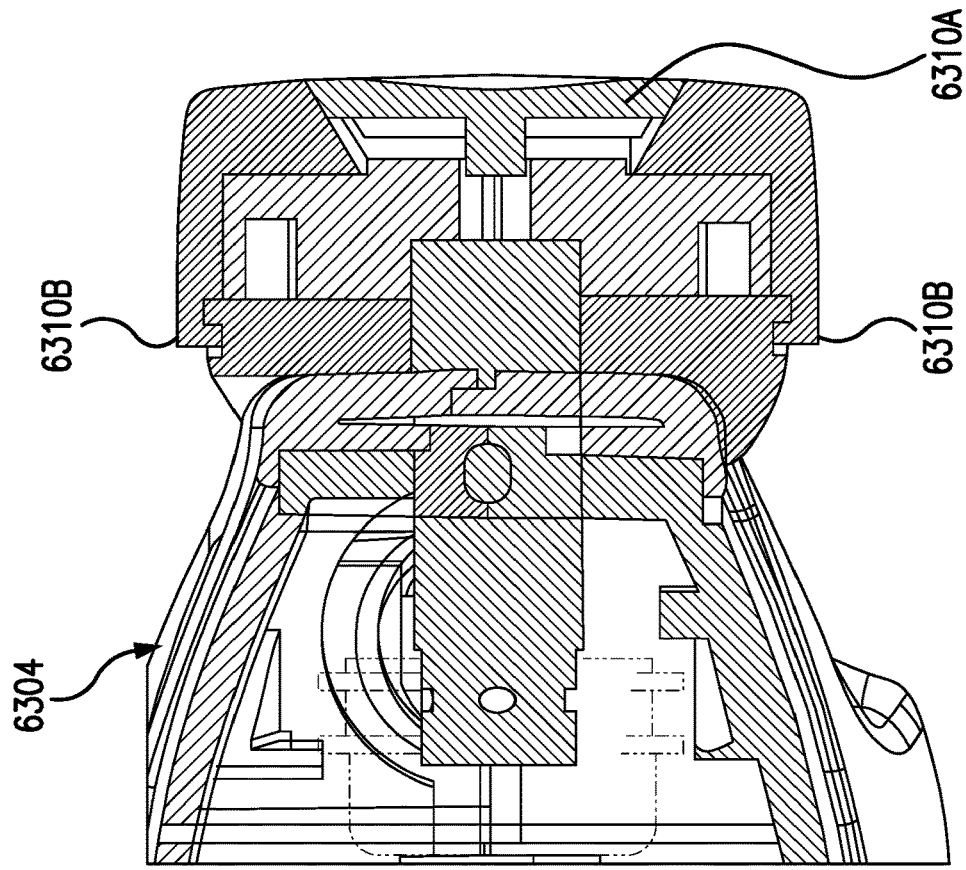

Although particular release assemblies for the lock line handle are described herein, this disclosure contemplates any suitable release assembly for the lock line handle. For example, and with reference to FIGS. 27A-28B, the release assembly can be a push-button release. FIG. 27A shows the lock line handle 6310 with the push button 6310A pressed and the lock line handle 6310 ready for removal from the handle 3604. FIG. 27B shows the lock line handle 6310 removed from the handle 6304. FIG. 28A shows a cut-away view of the push-button release 6310A in the locked position (i.e., preventing release of the lock line handle 6310). FIG. 28B shows a cut-away view of the push-button release 6310A in the unlock position (i.e., allowing release of the lock line handle). As shown, when push bottom release 6310A is pressed downwardly (arrow 6310C), flaps 6310B can extend outwardly (arrows 6310D), and release lock line handle 6310 from handle 6304.

Figure 29B:
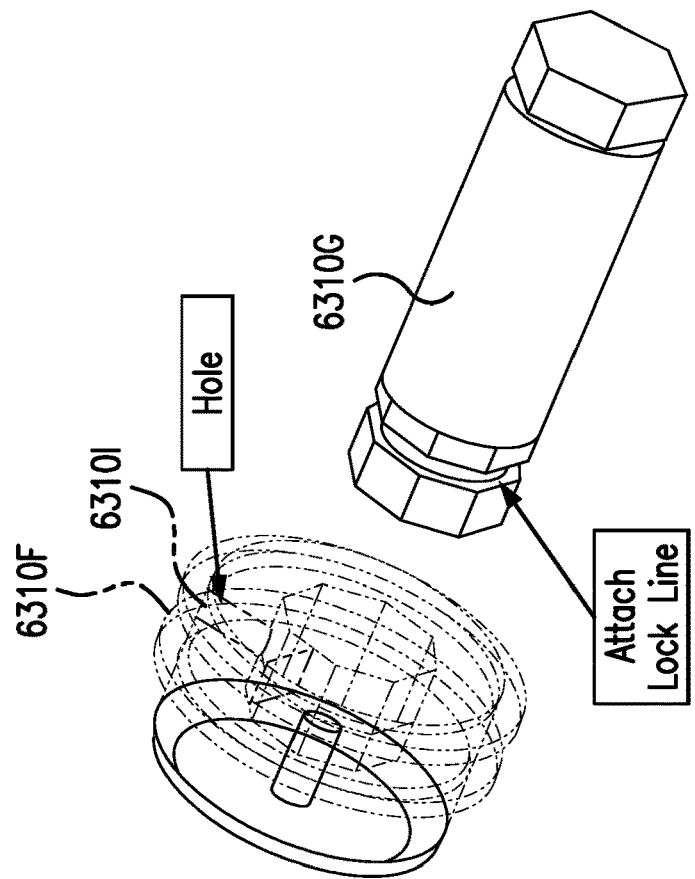
FIG. 29B is an exploded view of the spool and shaft of FIG. 29A.
Figure 29A:
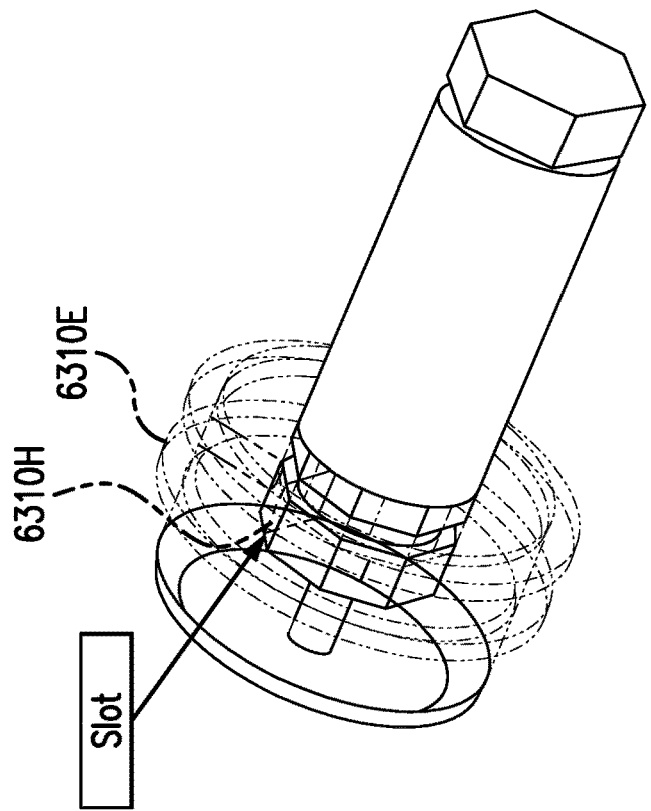
FIG. 29A is a perspective view of a spool and shaft of the lock line handle of FIG. 25A.
Figure 30:
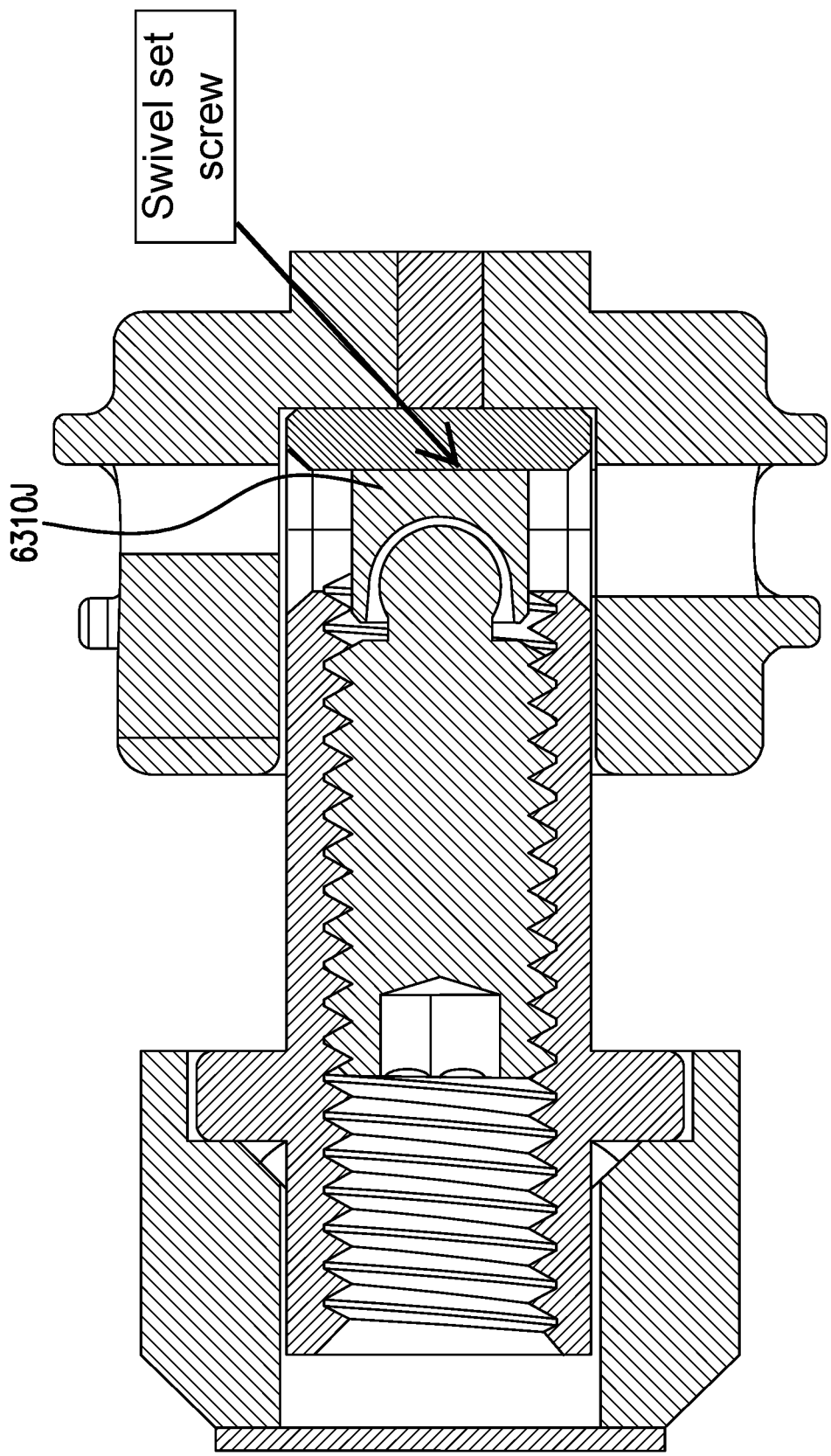
FIG. 30 is a cut-away view of a spool and swivel-head set screw of the lock line handle of FIG. 25A.

Although described particularly above, in accordance with the disclosed subject matter, the lock line can be coupled to the lock line handle in any suitable manner. For example, and with reference to FIGS. 29A and 29B, the lock line handle 6310 can include a spool 6310E for receiving the lock line 92. When the lock line handle is rotated, the lock line 92 can rotate around the spool 6310E. A first end portion of the lock line 92 can extend through a slot 6310H and can be attached to the shaft 6310G. A second end portion of the lock line can loop around spool 6310E, go through a hole 63101 in the spool 6310E, and can be trapped by the shaft 6310G. This loop can ensure the line does not slip during tensioning. During deployment, the shaft 6310G can be removed, as described above, which can free the second end portion of the lock line 92. Continuing to pull the shaft 6310G can pull the entire length of the lock line 92 out of the delivery system 300. With reference to FIG. 30, for purpose of illustration and not limitation, the first portion of the lock line can be fixedly coupled to the lock line handle 6310 by a swivel head set screw 6310J.

Although particular lock assemblies for the lock line handle are described herein, this disclosure contemplates any suitable lock assembly. Referring to FIGS. 31A-33 for purpose of illustration and not limitation, an exemplary lock line handle 7310 is provided. The lock line handle 7310 can include a lock assembly, for example, including activation lever 7310A for actuating a latch-detent lock. The latch-detent lock can prevent movement of the lock line handle between the lock and unlock positions unless the activation lever is actuated. The lock assembly can also prevent (or allow) movement between the unlock position and the third position. For example, the latch-detent lock can include a pin 7310B and detent 7310C disposed in track 7310D. The pin 7310B can engage the beginning or end of track (see e.g., FIG. 32A) or detent 7310B (see e.g., FIG. 32C). The lever of the lock assembly can control a latch-detent lock. FIG. 32A shows the lock line handle in the locked position with a latch-detent lock engaged. FIG. 32B shows the lock line handle in the unlock position with a latch-detent lock engaged. FIG. 32C shows a latch-detent lock disengaged to permit movement of the lock line handle 7310. Although the lock assembly includes a lever 7310A, the lock assembly can include any suitable activation feature, such as a button or switch. The lock line handle 7310 can also include a safety feature, for example a pin 7310E, to prevent premature actuation of the release assembly. FIG. 33 shows a pin 7310E that needs to be removed before the push-button release 7310F can be pressed to release the lock line handle 7310.

Figure 34:
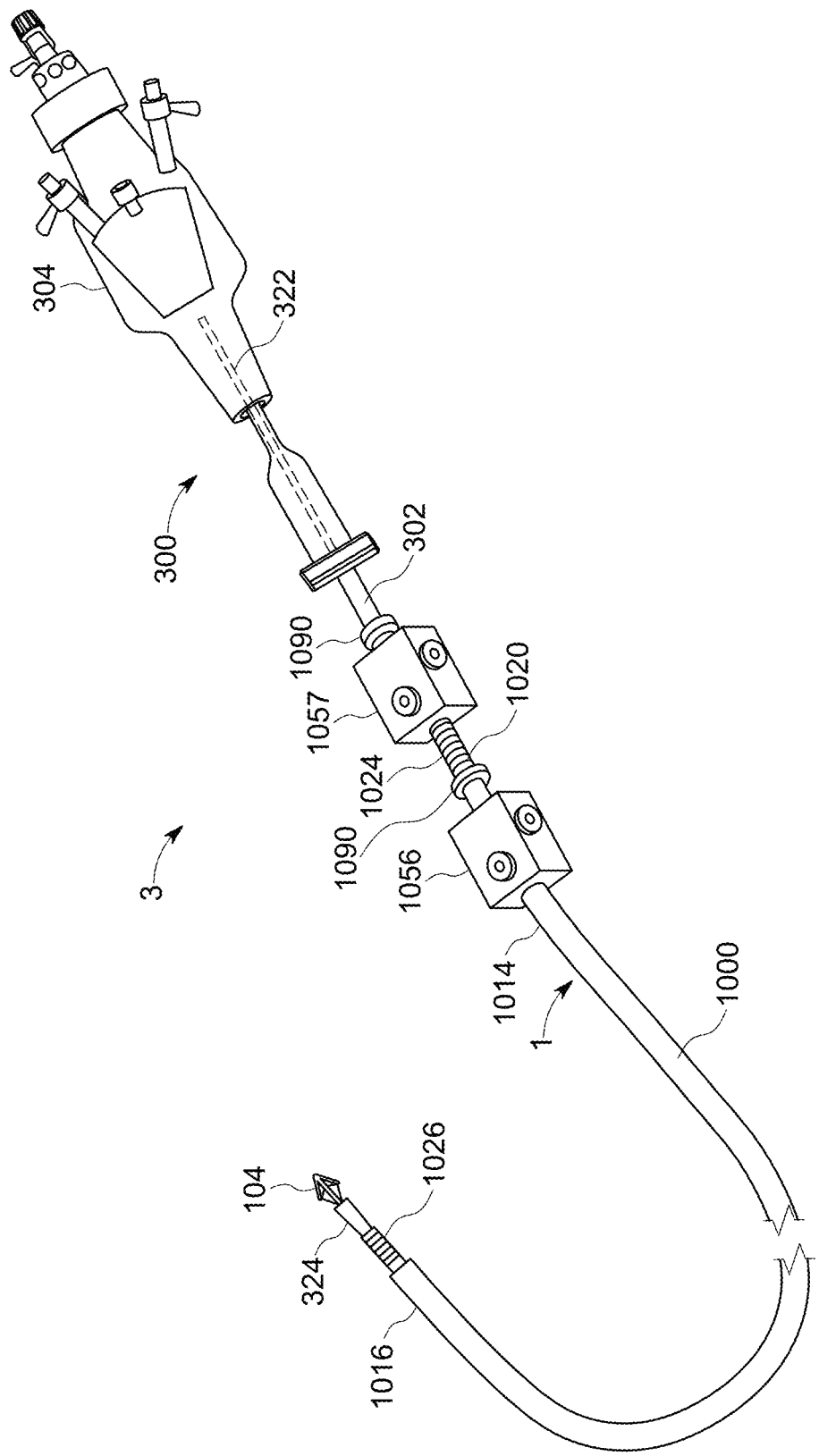
FIG. 34 is a perspective view of an exemplary embodiment of a delivery system in accordance with the disclosed subject matter.

Referring to FIG. 34, for purpose of illustration and not limitation, medical delivery system 3 including a steerable guide system 1 is provided. The steerable guide system 1 can include multiple steerable catheter components. For example, and not limitation, steerable guide system 1 can include an outer guide catheter 1000, having a proximal end 1014 and a distal end 1016, and an inner guide catheter 1020, having a proximal end 1024 and a distal end 1026, wherein the inner guide catheter 1020 is positioned coaxially within the outer guide catheter 1000, as shown. In addition, a hemostatic valve 1090 can be disposed within handle 1056 or external to handle 1056 as shown to provide leak-free sealing with or without the inner guide catheter 1020 in place. The distal ends 1016, 1026 of catheter 1000, 1020, respectively, are sized to be passable to a body cavity, typically through a body lumen such as a vascular lumen.

Manipulation of the guide catheter 1000, 1020 can be achieved with the use of handles 1056, 1057 attached to the proximal ends of the catheter 1000, 1020. As shown, handle 1056 is attached to the proximal end 1014 of outer guide catheter 1000 and handle 1057 is attached to the proximal end 1024 of inner guide catheter 1020. Inner guide catheter 1020 is inserted through handle 1056 and is positioned coaxially within outer guide catheter 1000.

The delivery catheter 300 can be inserted though handle 1057 and can be positioned coaxially within inner guide catheter 1020 and outer guide catheter 1000. The delivery catheter 300 includes a shaft 302, having a proximal end 322 and a distal end 324, and a handle 304 attached to the proximal end 322. A fixation device 104 can be removably coupled to the distal end 324 for deliver to a site within the patient The outer guide catheter 1000 and/or the inner guide catheter 1020 can be precurved and/or have steering mechanisms to position the distal ends 1016, 1026 in desired directions. Precurvature or steering of the outer guide catheter 1000 can direct the distal end 1016 in a first direction to create a primary curve while precurvature and/or steering of the inner guide catheter 1020 can direct distal end 1026 in a second direction, different from the first, to create a secondary curve. Together, the primary and secondary curves can form a compound curve. Furthermore, advancement of the entire interventional system 3 or the inner guide catheter 1020 (relative to the outer guide catheter 1000) can further direct the distal end 1026 of the inner guide catheter 1020 toward a desired position. Advancement of the delivery catheter 300 through the coaxial guide catheters 1000, 1020 can guide the delivery catheter 300 through the compound curve toward a desired direction, usually in a direction which will position the fixation device 104 in a desired location in the body.

Figure 35:
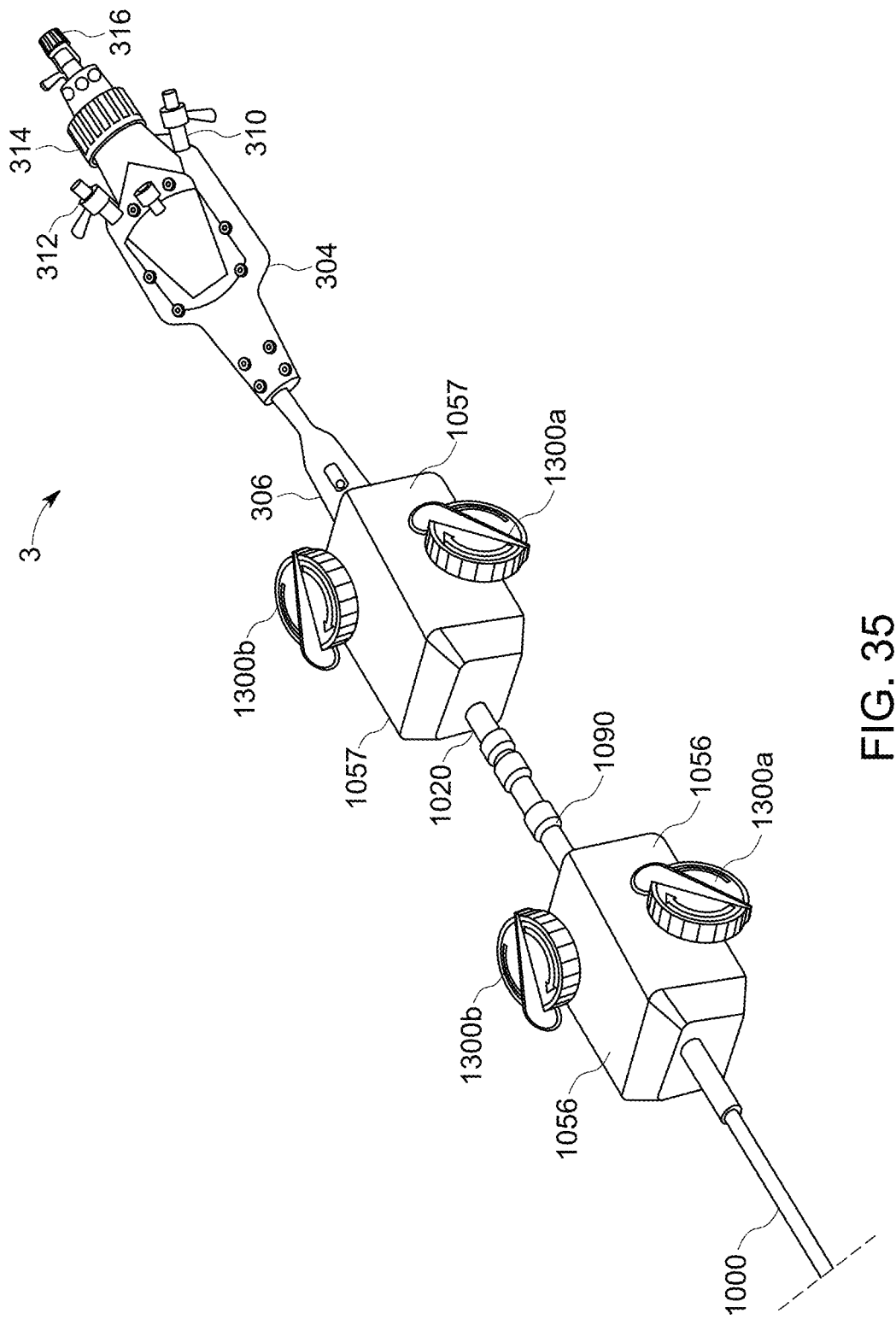
FIG. 35 is an enlarged perspective view of a portion of the exemplary embodiment of a delivery system in accordance with the disclosed subject matter.

FIG. 35 is an enlarged view of the controls of a medical delivery system 3 in accordance with the disclosed subject matter. Handles 1056, 1057 of the steerable guide system 1 are shown. Each handle 1056, 1057 includes a set of steering knobs 1300a, 1300b, as shown. Manipulation of guide catheter 1000 and 1020 can be achieved with the use of the steering knobs 1300a, 1300b attached to the proximal ends of the catheters 1000, 1020. Further details of exemplary delivery systems are disclosed in the patents and published applications incorporated by reference herein. Alternative handles and/or controls likewise are contemplated in accordance with the disclosed subject matter.

While the embodiments disclosed herein utilize a push-to-open, pull-to-close mechanism for opening and closing arms it should be understood that other suitable mechanisms can be used, such as a pull-to-open, push-to-close mechanism. A closure bias can be included, for example using a compliant mechanism such as a linear spring, helical spring, or leaf spring. Other actuation elements can be used for deployment of the gripper elements.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A medical device delivery system for delivering a medical implant, comprising:
   a catheter having a proximal end portion and a distal end portion;
   a handle coupled to the proximal end portion of the catheter;
   a lock line handle releasably coupled to the handle;
   a lock line having a first end portion fixedly coupled to the lock line handle and a second end portion releasably coupled to the lock line handle by a releasable lock, wherein the second end portion is configured to be released from the lock line handle by release of the lock line handle from the handle; and
   a release assembly comprising a release mechanism configured to release the lock line handle from the handle, the release mechanism disposed on and at least partially exposed outside the handle separate from the lock line handle.

2. The medical device delivery system of claim 1, wherein the release mechanism is a slide release, a clip, a snap fit, or a button-release.

3. The medical device delivery system of claim 2, wherein the release mechanism is a button-release comprising at least one tab configured to be depressed to decouple the lock line handle from the handle.

4. The medical device delivery system of claim 1, wherein the release assembly comprises a first lock member and a second lock member releasably coupled to the first lock member, wherein the release mechanism is configured to uncouple the first lock member and the second lock member.

5. The medical device delivery system of claim 1, wherein the lock line handle comprises a spool to wind the lock line.

6. The medical device delivery system of claim 5, wherein
   the lock line handle further comprises a shaft releasably coupled with the spool;
   the second end portion of the lock line is captured between the spool and the shaft; and
   release of the lock line handle from the handle allows the second end portion of the lock line to be released from between the spool and the shaft.

7. The medical device delivery system of claim 1, wherein:
   the lock line handle is configured to be moved between a lock position and an unlock position; and
   further wherein actuating from the lock position toward the unlocked position increases a tension on the lock line, and
   actuating the lock line handle from the unlock position toward the lock position decreases the tension on the lock line.

8. The medical device delivery system of claim 7, wherein each of increasing and decreasing the tension on the lock line is achieved by rotating the lock line handle.

9. The medical device delivery system of claim 7, further comprising a lock assembly configured to selectively secure the lock line handle in each of the lock position and unlock position.

10. The medical device delivery system of claim 9, wherein the lock assembly comprises at least one of audible and tactile feedback upon locking.

11. The medical device delivery system of claim 9, wherein the lock assembly comprises a latch-detent lock.

12. The medical device delivery system of claim 11, wherein the lock assembly includes:
   a plurality of detents along a surface of the lock line handle, and a spring-biased pin to engage with the plurality of detents.

13. The medical device delivery system of claim 9, wherein the lock line handle is actuatable from the unlock position toward a third position to further increase tension on the lock line beyond the tension on the lock line in the unlock position.

14. The medical device delivery system of claim 13, further comprising an override mechanism to selectively prevent actuation of the lock line handle from the unlock position to the third position.

15. The medical device delivery system of claim 7, wherein the lock line handle further comprises a gear set to apply the tension on the lock line.

16. The medical device delivery system of claim 7, wherein the lock line handle is configured to translate linearly relative the handle to actuate between the lock position and the unlock position.

17. The medical device delivery system of claim 16, wherein the lock line handle is a T-shape, a thumb slide, or a pear shape.

18. The medical device delivery system of claim 1, wherein the catheter defines at least one lumen extending between the proximal end portion and the distal end portion; and
   the medical device delivery system further comprises a shaft having a proximal end portion and a distal end portion, and extending through the at least one lumen, the medical implant releasably coupled the distal end portion of the shaft.

19. The medical device delivery system of claim 1, wherein the medical implant comprises an implantable fixation device including
 a first arm moveable between a first position and a second position;
 a second arm moveable between a first position and a second position;
 wherein when the lock line handle is in a lock position the first arm and the second arm are restricted at least from moving from the respective first positions toward the respective second positions, and further wherein when the lock line handle is in an unlock position the first arm and second arm can be moved freely between the respective first positions and respective second positions.

20. The medical device delivery system of claim 9, wherein when the lock line handle is in the lock position, the first arm and the second arm can each move from the respective second positions toward the respective first positions.

* * * * *